(12) United States Patent
Min

(10) Patent No.: US 7,702,390 B1
(45) Date of Patent: Apr. 20, 2010

(54) RATE ADAPTIVE BIVENTRICULAR AND CARDIAC RESYNCHRONIZATION THERAPY

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 638 days.

(21) Appl. No.: 11/610,175

(22) Filed: Dec. 13, 2006

(51) Int. Cl.
*A61N 1/365* (2006.01)
(52) U.S. Cl. ......................................... 607/9
(58) Field of Classification Search .................. 607/7, 607/9, 17
See application file for complete search history.

(56) References Cited

U.S. PATENT DOCUMENTS

| | | |
|---|---|---|
| 4,712,555 A | 12/1987 | Thornander et al. |
| 4,788,980 A | 12/1988 | Mann et al. |
| 4,928,688 A | 5/1990 | Mower |
| 4,940,052 A | 7/1990 | Mann et al. |
| 4,944,298 A | 7/1990 | Sholder |
| 5,086,774 A | 2/1992 | Duncan |
| 5,174,289 A | 12/1992 | Cohen |
| 5,179,949 A | 1/1993 | Chirife |
| 5,391,189 A | 2/1995 | van Krieken et al. |
| 5,466,254 A | 11/1995 | Helland |
| 5,476,483 A | 12/1995 | Bornzin et al. |
| 5,643,327 A | 7/1997 | Dawson et al. |
| 5,741,308 A | 4/1998 | Sholder |
| 5,749,906 A | 5/1998 | Kieval et al. |
| 5,800,465 A | 9/1998 | Thompson et al. |
| 5,814,077 A | 9/1998 | Sholder et al. |
| 5,814,089 A | 9/1998 | Stokes et al. |
| 5,873,895 A | 2/1999 | Sholder et al. |
| 6,122,546 A | 9/2000 | Sholder et al. |
| 6,141,588 A | 10/2000 | Cox et al. |
| 6,144,880 A | 11/2000 | Ding et al. |
| 6,285,907 B1 | 9/2001 | Kramer et al. |

(Continued)

FOREIGN PATENT DOCUMENTS

EP 0494487 B1 1/1996

(Continued)

OTHER PUBLICATIONS

Chirife, R. et al., "Nonphysiological Left Heart AV Intervals as a Result of DDD and AAI "Physiological" Pacing," PACE 1991;14(Pt. II):1752-1756.

(Continued)

*Primary Examiner*—George R Evanisko
*Assistant Examiner*—Michael D'Abreu

(57) ABSTRACT

An exemplary implantable device includes control logic to determine a base state atrio-ventricular delay (e.g., PV base or AV base) based on width of an atrial event (e.g., $\Delta P$ or $\Delta A$) as measured during a patient base state and based on a value of a parameter $\delta$ that depends on the atrial event and control logic to determine an active state atrio-ventricular delay (e.g., PV active or AV active) based at least in part on a base state interval (e.g., DD base or AD base) measured during a patient base state and an active state interval (e.g., DD active or AD active) measured during a patient active state where such intervals extend from the end of a respective atrial event to the beginning of a respective ventricular QRS complex or a point within a respective ventricular QRS complex. Various other exemplary methods, devices, systems, etc., are also disclosed.

4 Claims, 20 Drawing Sheets

U.S. PATENT DOCUMENTS

| | | |
|---|---|---|
| 6,314,323 B1 | 11/2001 | Ekwall |
| 6,360,127 B1 | 3/2002 | Ding et al. |
| 6,411,848 B2 | 6/2002 | Kramer et al. |
| 6,424,865 B1 | 7/2002 | Ding |
| 6,473,645 B1 | 10/2002 | Levine |
| 6,473,647 B1 | 10/2002 | Bradley |
| 6,496,730 B1 | 12/2002 | Kleckner et al. |
| 6,567,700 B1 | 5/2003 | Turcott et al. |
| 6,606,516 B2 | 8/2003 | Levine |
| 6,622,040 B2 | 9/2003 | Ding et al. |
| 6,668,194 B2 | 12/2003 | VanHout |
| 6,754,530 B2 | 6/2004 | Bakels et al. |
| 6,804,555 B2 | 10/2004 | Warkentin |
| 6,934,586 B2 | 8/2005 | Struble et al. |
| 6,959,214 B2 | 10/2005 | Pape et al. |
| 7,203,541 B2 | 4/2007 | Sowelam et al. |
| 7,248,925 B2 | 7/2007 | Bruhns et al. |
| 2001/0016759 A1 | 8/2001 | Kramer et al. |
| 2001/0031993 A1 | 10/2001 | Salo et al. |
| 2002/0049478 A1 | 4/2002 | Ding et al. |
| 2002/0062139 A1 | 5/2002 | Ding |
| 2002/0077559 A1 | 6/2002 | Ding et al. |
| 2002/0161410 A1 | 10/2002 | Kramer et al. |
| 2003/0004548 A1 | 1/2003 | Warkentin |
| 2003/0014084 A1 | 1/2003 | VanHout |
| 2003/0060851 A1 | 3/2003 | Kramer et al. |
| 2003/0130702 A1 | 7/2003 | Kramer et al. |
| 2003/0195580 A1 | 10/2003 | Bradley et al. |
| 2003/0204212 A1 | 10/2003 | Burnes et al. |
| 2004/0133246 A1 | 7/2004 | Ding et al. |
| 2004/0147966 A1 | 7/2004 | Ding et al. |
| 2004/0193223 A1 | 9/2004 | Kramer et al. |
| 2005/0090870 A1 | 4/2005 | Hine et al. |
| 2005/0149138 A1 | 7/2005 | Min et al. |

FOREIGN PATENT DOCUMENTS

| | | | |
|---|---|---|---|
| EP | 1199085 A2 | | 4/2002 |
| EP | 1234597 A2 | | 8/2002 |
| WO | WO99/58191 | | 11/1999 |
| WO | WO 02/051495 A2 | | 7/2002 |
| WO | WO03/037427 A1 | | 5/2003 |
| WO | WO 2005/039690 A1 | | 5/2005 |

OTHER PUBLICATIONS

Chirife, Raul et al., "Automatic Beat-To-Beat Left Heart AV Normalization: Is it Possible?", PACE 2003;26:2103-2110.

Chirife, Raul, "Proposal of a Method for Automatic Optimization of Left Heart Atrioventricular Interval Applicable to DDD Pacemakers", PACE 1995;18(Pt. 1):49-56.

Chirife, R. M.D., Letters to the Editor, PACE 2000;23:92.

Ebner, Erich et al., "Ventricular Evoked Response as Clinical Marker for Hemodynamic Changes in Dilative Cardiomyopathy," PACE 2004;27:166-174.

Ishikawa, Toshiyuki et al., "Prediction of Optimal Atrioventricular Delay in Patients with Implanted DDD Pacemakers", PACE Sep. 1999;22:1365-1371.

Ismer, B. et al., "Impact of Discriminating Electrophysiological and Electromechanical Determinants of the Optimal AV Delay in Right and Biventricular DDD Pacing", Folia Cardiol. 2006, tom 13, supl. C.

Schreier, G. et al., "Correlation Between Changes in Stroke Volume and the Paced Intracardiac Electrogram," Europace 2002;4:303-310.

Schuchert, Andreas et al., "Effects of Body Position and Exercise on Evoked Response Signal for Automatic Threshold Activation," PACE 1999;22:1476-1480.

NonFinal Office Action, mailed Nov. 17, 2005: U.S. Appl. No. 10/703,070.

Final Office Action, mailed Jul. 31, 2006: U.S. Appl. No. 10/703,070.

Advisory Action, mailed Oct. 20, 2006: U.S. Appl. No. 10/703,070.

NonFinal Office Action, mailed Apr. 10, 2007: U.S. Appl. No. 10/703,070.

NonFinal Office Action, mailed Apr. 10, 2007: U.S. Appl. No. 10/974,123.

NonFinal Office Action, mailed Jul. 31, 2006: U.S. Appl. No. 10/986,273.

Final Office Action, mailed Jul. 16, 2007: U.S. Appl. No. 10/986,273.

NonFinal Office Action, mailed Oct. 9, 2007: U.S. Appl. No. 10/980,140.

Merino, J.L. MD et al., "Bundle-Branch Reentry and the Postpacing Interval After Entrainment by Right Ventricular Apex Stimulation," Circulation (2001), pp. 1102-1108.

Nelson, G.S. PhD. et al., "Left Ventricular or Biventricular Pacing Improves Cardiac Function at Diminished Energy Cost in Patients with Dilated Cardiomyopathy and left Bundle-Branch Block," Circulation (2000), pp. 3053-3059.

Gerber, T.C. MD et al., "Left Ventricular and Biventricular Pacing in Congestive Heart Failure," Mayo Clinic Proc. (2001), vol. 76, pp. 803-812.

Wang, Paul et al., "Timing Cycles for Biventricular Pacing," PACE, 2002; vol. 25(1), pp. 62-75.

EXEMPLARY AR RHYTHMS
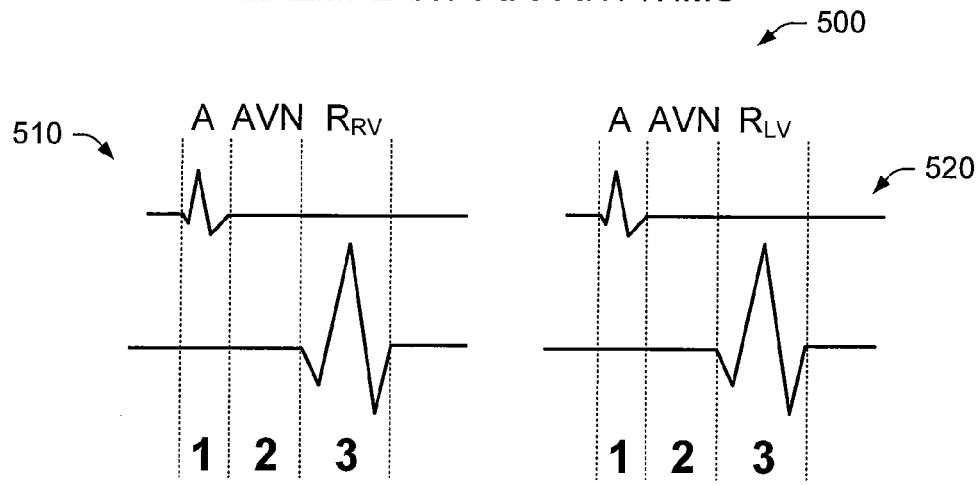
$AR_{RV} = R_{RV} - A$      $AR_{LV} = R_{LV} - A$
$\Delta = AR_{LV} - AR_{RV}$
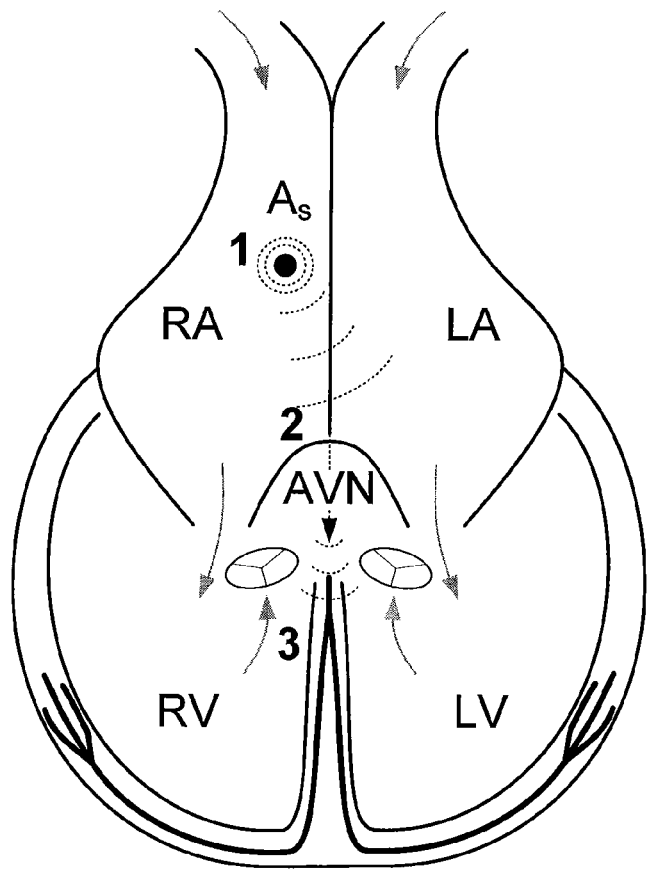
Fig.5

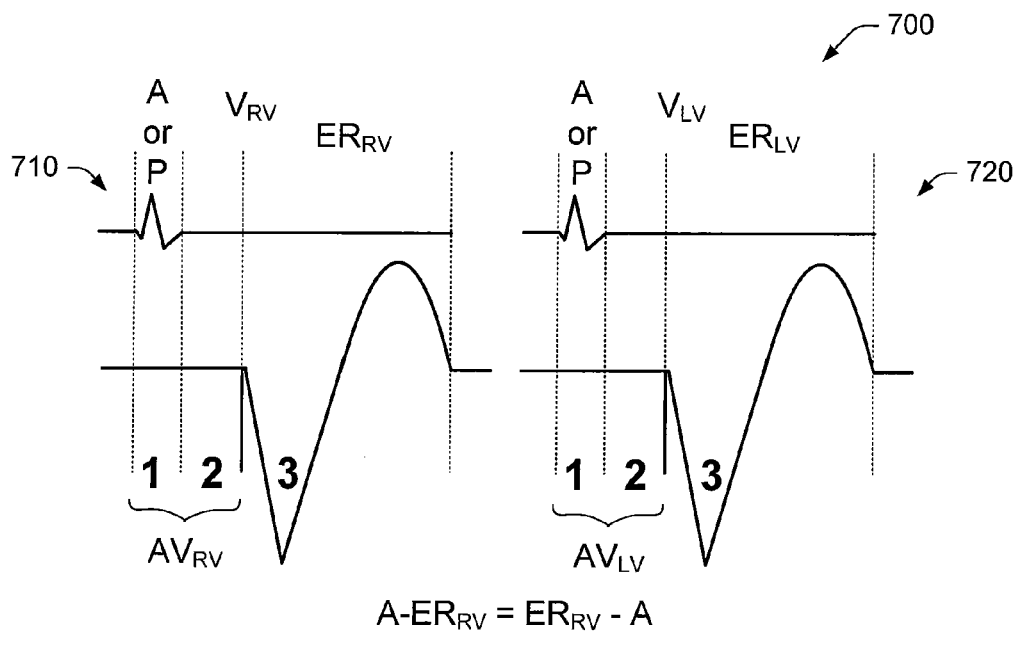
$A\text{-}ER_{RV} = ER_{RV} - A$
$A\text{-}ER_{LV} = ER_{LV} - A$
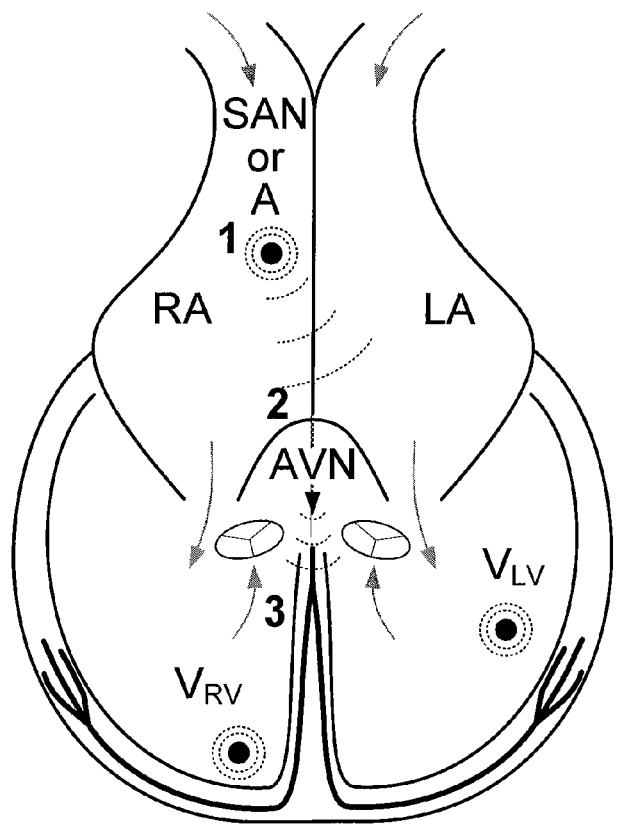
Fig.7

Exemplary Methods 1200

States 1210

$AS_0$ = Base State (e.g., Rest)
$AS_1$ = Active State 1
$AS_2$ = Active State 2
$AS_N$ = Active State N

PV or AV States 1220

$\beta = \delta/DD(AS_0)$
$\beta = \delta/AD(AS_0)$ $\delta = f(\Delta P(AS_0))$ $\delta = f(\Delta A(AS_0))$
$\delta = f(\Delta P(AS_x))$ $\delta = f(\Delta A(AS_x))$ $PV(AS_0) = \Delta P(AS_0) + \delta$
$AV(AS_0) = \Delta A(AS_0) + \delta$ $PV(AS_x) = \Delta P(AS_x) + \beta*DD(AS_x)$
$AV(AS_x) = \Delta A(AS_x) + \beta*AD(AS_x)$ $PV(AS_0) = \Delta P(AS_0) + \delta - PL$
$AV(AS_0) = \Delta A(AS_0) + \delta - PL$ $PV(AS_x) = \Delta P(AS_x) + \beta*DD(AS_x) - PL$
$AV(AS_x) = \Delta A(AS_x) + \beta*AD(AS_x) - PL$

VV States 1230

$\alpha$ = Constant
$\alpha = \alpha(AS_0)$
$\alpha = \alpha(AS_x)$ $\Delta(AS_0) = R_{LV}(AS_0) - R_{RV}(AS_0)$
$\Delta(AS_x) = R_{LV}(AS_x) - R_{RV}(AS_x)$ $\Delta_{IVCD}(AS_0) = IVCD-LR(AS_0) - IVCD-RL(AS_0)$
$\Delta_{IVCD}(AS_x) = IVCD-LR(AS_x) - IVCD-RL(AS_x)$ $VV(AS_0) = \alpha*(\Delta(AS_0) + \Delta_{IVCD}(AS_0))$
$VV(AS_x) = \alpha*(\Delta(AS_x) + \Delta_{IVCD}(AS_x))$ $VV(AS_0) = \alpha*(\Delta(AS_0) + \Delta_{IVCD}(AS_0)) - \Delta PL$
$VV(AS_x) = \alpha*(\Delta(AS_x) + \Delta_{IVCD}(AS_x)) - \Delta PL$

Fig. 12

RATE ADAPTIVE BIVENTRICULAR AND CARDIAC RESYNCHRONIZATION THERAPY

RELATED APPLICATIONS

This application is related to U.S. patent application Ser. No. 10/703,070 filed on Nov. 5, 2003, entitled METHODS FOR VENTRICULAR PACING, and the specification thereof is incorporated herein by reference. This application is also related to co-filed U.S. patent application Ser. No. 11/610,175 entitled RATE ADAPTIVE BIVENTRICULAR AND CARDIAC RESYNCHRONIZATION THERAPY.

TECHNICAL FIELD

Exemplary technologies presented herein generally relate to cardiac pacing and/or stimulation therapy. Various techniques adjust pacing therapy based on patient activity.

BACKGROUND

Clinical studies related to cardiac pacing have shown that an optimal atrio-ventricular delay (e.g., AV delay) and/or an optimal interventricular delay (e.g., VV delay) can improve cardiac performance. However, such optimal delays depend on a variety of factors that may vary over time. Thus, what is "optimal" may vary over time. An optimization of AV delay and/or VV delay may occur at implantation and sometimes, a re-optimization may occur during a follow-up consultation. While such optimizations are beneficial, the benefits may not be long lasting due to changes in various factors related to device and/or cardiac function. As described herein, various exemplary methods, devices and/or systems aim to determine and/or adjust AV delay, VV delay and/or other interchamber delays.

SUMMARY

An exemplary implantable device includes control logic to determine a base state atrio-ventricular delay (e.g., PV base or AV base) based on width of an atrial event (e.g., $\Delta P$ or $\Delta A$) as measured during a patient base state and based on a value of a parameter $\delta$ that depends on the atrial event and control logic to determine an active state atrio-ventricular delay (e.g., PV active or AV active) based at least in part on a base state interval (e.g., DD base or AD base) measured during a patient base state and an active state interval (e.g., DD active or AD active) measured during a patient active state where such intervals extend from the end of a respective atrial event to the beginning of a respective ventricular QRS complex or a point within a respective ventricular QRS complex. Various other exemplary methods, devices, systems, etc., are also disclosed. In general, the various methods, devices, systems, etc., described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

FIG. 5 is an approximate anatomical diagram of a heart and two IEGM waveforms that exhibit an A wave and an R wave.

FIG. 7 is an approximate anatomical diagram of a heart and two sets of IEGM waveforms that include an A or P wave on an atrial sensing channel and evoked response on a ventricular sensing channel.

FIG. 12 is a series of equations for use in various exemplary methods for single ventricular pacing and/or bi-ventricular pacing therapies.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used at times to reference like parts or elements throughout the description.

Overview

Exemplary techniques pertain generally to ventricular pacing. For example, various exemplary methods include deciding whether to use ventricular pacing and, if so, whether to pace in a single ventricle or in both ventricles. If such a method decides that ventricular pacing is appropriate, then the method may also determine an atrio-ventricular delay for one or both ventricles. For the case of bi-ventricular pacing, the method may determine an atrio-ventricular delay for each ventricle and/or an interventricular delay (e.g., which may be inherent in the use of two atrio-ventricular delay times). Such methods may use information about patient activity to determine one or more pacing parameters such as AV, PV and/or VV.

The following description begins with a discussion of exemplary implantable devices and associated components followed by a discussion of heart rhythms and associated waveforms. Next, a discussion of cardiac performance follows, and the detailed description continues with a discussion of various exemplary methods, devices, systems, etc.

Exemplary Stimulation Device

The techniques described below are intended to be implemented in connection with any stimulation device that is configured or configurable to stimulate nerves and/or stimulate and/or shock a patient's heart.

Figure 1:
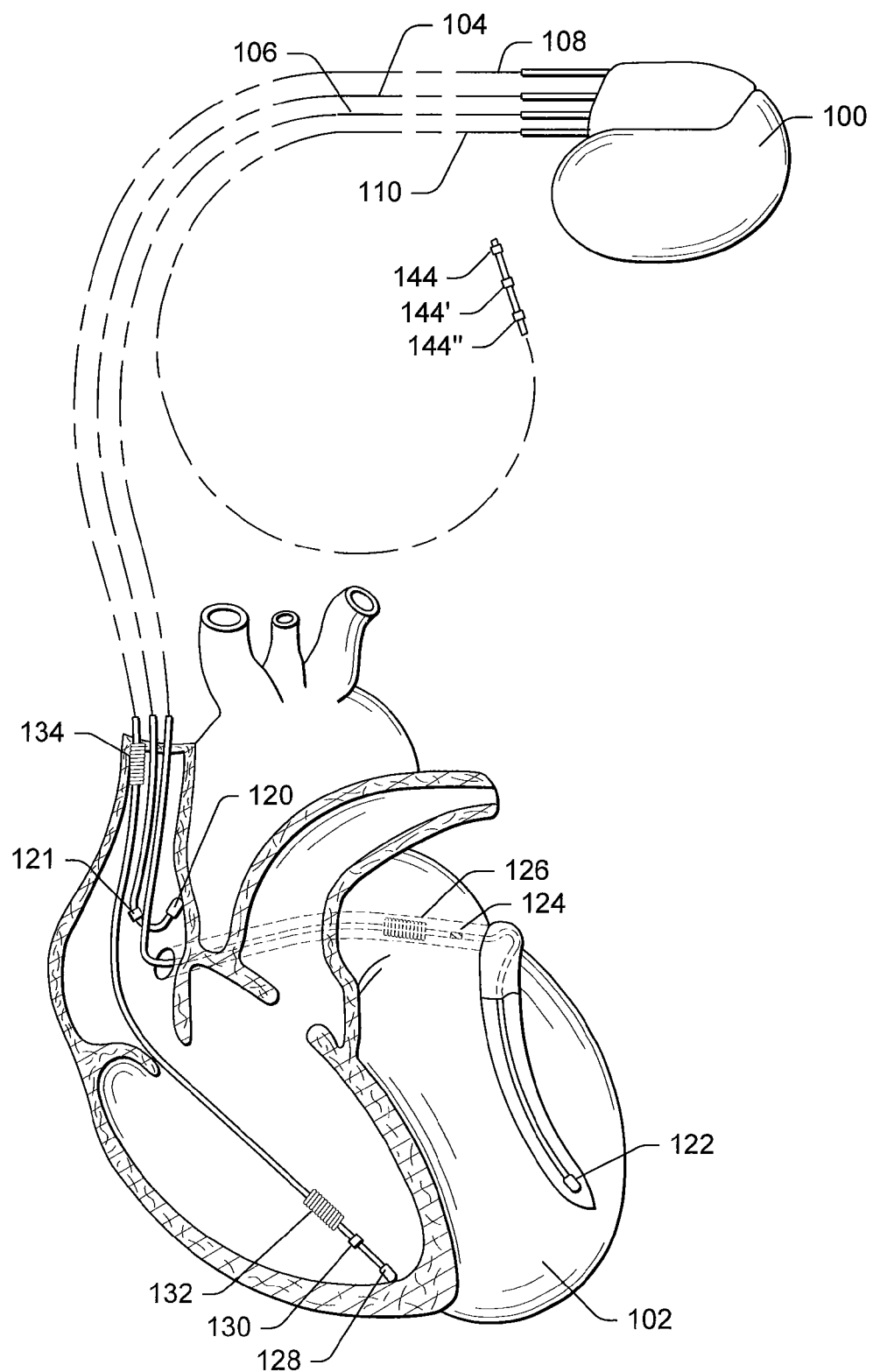
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
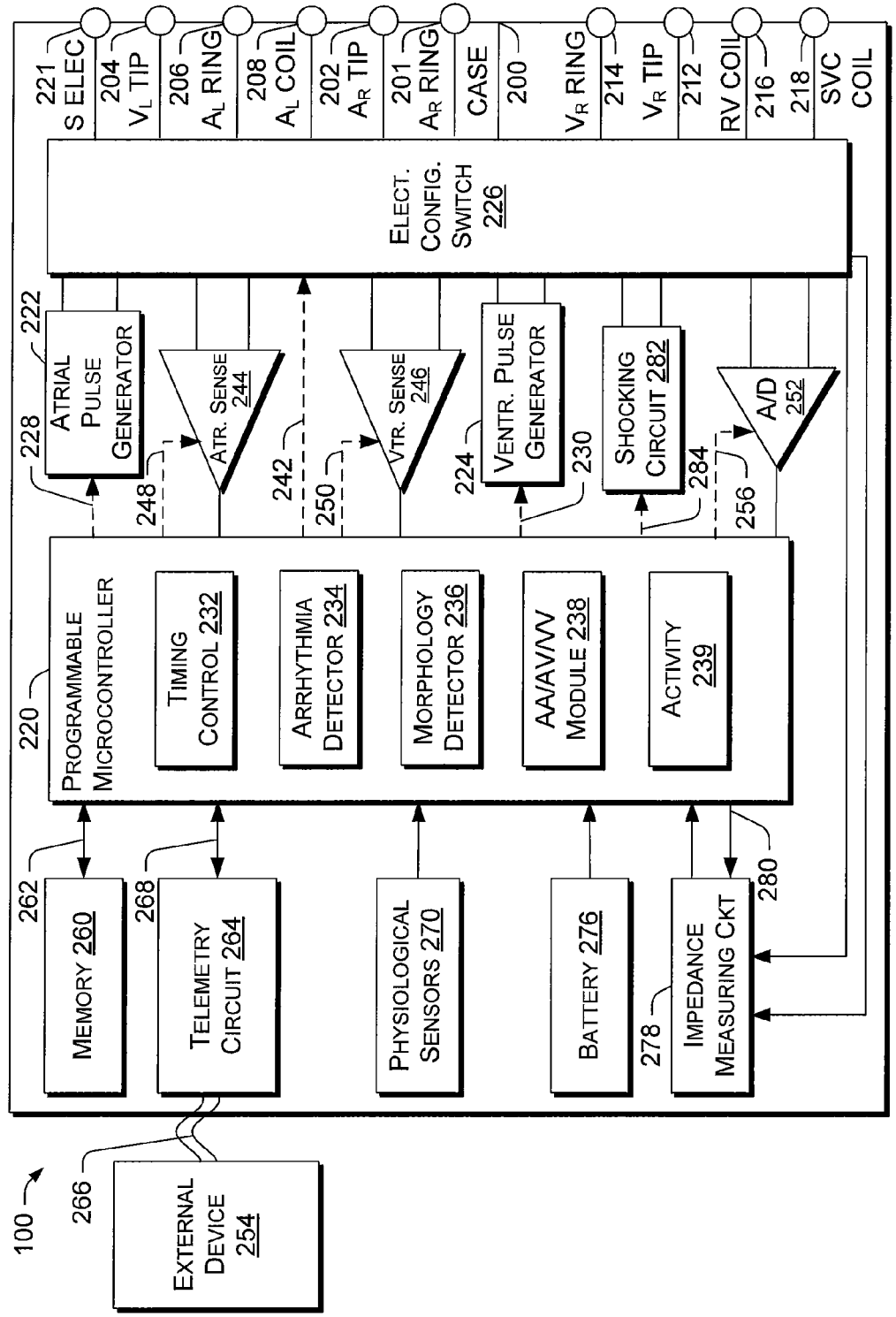
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (e.g., AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, bi-ventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays. Such a module may help make determinations as to fusion.

The microcontroller 220 of FIG. 2 also includes an activity module 239. This module may include control logic for one or more activity related features. For example, the module 239 may include an algorithm for determining patient activity level, calling for an activity test, calling for a change in one or more pacing parameters, etc. These algorithms are described in more detail with respect to the figures. The module 239 may be implemented in hardware as part of the microcontroller 220, or as software/firmware instructions programmed into the device and executed on the microcontroller 220 during certain modes of operation. The module 239 may act cooperatively with the AA/AV/VV module 238.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Heart Rhythms

Figure 3:
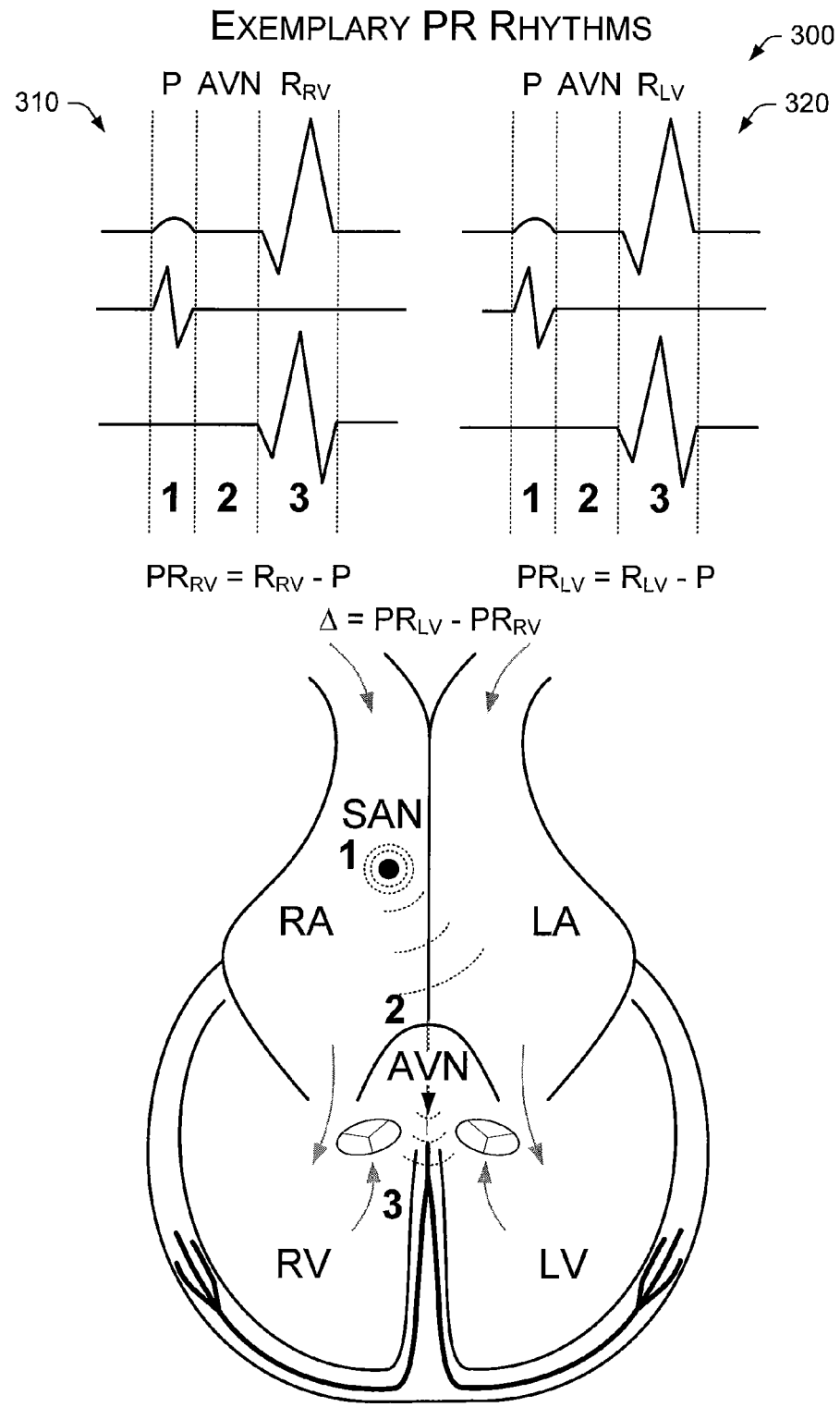
FIG. 3 is an approximate anatomical diagram of a heart, a surface ECG and two IEGM waveforms that exhibit an intrinsic P wave and an R wave.

FIG. 3 shows an approximate anatomical diagram of a heart and two sets of PR waveforms 300. One set of waveforms 310 corresponds in part to right ventricular activity while another set of waveforms 320 corresponds in part to left ventricular activity. Action potentials propagating through a normal heart are labeled as follows: 1, associated with the sinoatrial node (SAN) and the atria; 2, associated with the atrio-ventricular node (AVN); and 3, associated with right and left bundle branches of the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

FIG. 3 also shows two surface electrocardiograms (ECG) of normal heart activity (e.g., polarization, depolarization, etc.) wherein atrial depolarization is represented as a "P wave" and ventricular depolarization is represented as an "R wave", or QRS complex. The right ECG shows a P wave followed by an AVN conduction delay (AVN) and a right ventricular R wave or QRS complex ($R_{RV}$). The left ECG shows a P wave followed by an AVN conduction delay (AVN) and a left ventricular R wave or QRS complex ($R_{LV}$). In this example, the right and left ventricular R waves ($R_{RV}$ and $R_{LV}$) are due to conduction through the atrio-ventricular node and not due to artificially paced events. The sets of plots 310, 320 include approximate atrial IEGM waveforms and approximate ventricular IEGM waveforms, for example, as sensed by an atrial sensing channel and one or more ventricular sensing channels.

Often detection of an R wave or QRS complex in an IEGM relies on signal amplitude or signal derivative with respect to time. Further, many detection methods are capable of assigning a time to a detected R wave or QRS complex or assigning a time span to a P wave to R wave or QRS complex interval, which are shown in FIG. 3 as $PR_{RV}$ for the right ventricle and $PR_{LV}$ for the left ventricle. Measurement of the PR interval typically relies on measurement of the beginning of a P wave, as opposed to end of a P wave, which is discussed below with respect to an interval labeled "DD". Again, the "R" of the PR interval is typically the beginning of a QRS complex or a feature of an R wave.

If $PR_{RV}$ and $PR_{LV}$ are approximately equal, then the right ventricle and the left ventricle contract in a synchronous manner. For example, in a normal heart, the delay between contraction of the right ventricle and the left ventricle may be around 5 ms. However, if $PR_{RV}$ and $PR_{LV}$ differ substantially, e.g., $|\Delta|=|PR_{LV}-PR_{RV}|>5$ ms, then the right ventricle and left ventricle contract in an asynchronous manner, which may indicate some degree of cardiac dysfunction. Depending on patient or other factors, the time could be set at some time other than 5 ms.

The variable $\Delta$ represents an interventricular delay that is based on an atrio-ventricular delay for the left ventricle ($PR_{LV}$) and an atrio-ventricular delay for the right ventricle ($PR_{RV}$). The variable $|\Delta|$ is shown as the absolute value of the difference while herein and in the figures the variable $\Delta$ (e.g., $\Delta=PR_{LV}-PR_{RV}$) may be less than zero when $PR_{RV}$ exceeds $PR_{LV}$ or greater than zero when $PR_{LV}$ exceeds $PR_{RV}$. Described further below is a variable referred to as a paced interventricular conduction delay ($\Delta_{PIVCD}$), which relies on pacing in one ventricle and sensing in the other ventricle and optionally vice versa. In general, the term "atrio-ventricular" delay may pertain to an AV delay, a PV delay, an AR delay or a PR delay.

With respect to cardiac condition, a long interventricular delay may be indicative of a conduction block. For example, left bundle branch block (LBBB) may cause the left ventricle to contract more than approximately 50 ms after contraction of the right ventricle (e.g., $\Delta>0$). Whereas a right bundle branch block (RBBB) may be expected to cause the right ventricle to contract well after the left ventricle (e.g., $\Delta<0$). Of course, a patient may have RBBB and LBBB of similar extent such that interventricular delay does not indicate whether a block could be RBBB or LBBB. In such circumstances, atrio-ventricular delay may indicate block. For example, an atrio-ventricular delay of more than approximately 200 ms in a non-atrial paced heart may indicate some degree of block or conduction problem while an atrio-ventricular delay of more than approximately 250 ms in an atrial paced heart may indicate some degree of block or conduction problem.

As inferred in the Background section, significant asynchronous ventricular contraction (e.g., non-optimal VV delay) may in some instances impair cardiac function. Thus, where a patient has an interventricular delay that would result in significant asynchronous contraction, various exemplary methods, devices and/or systems described herein may treat such a cardiac condition and reduce deleterious effects associated with such the condition. Hence, various exemplary methods that pace in response to right and left ventricular conduction asymmetries may improve cardiac function.

Figure 4:
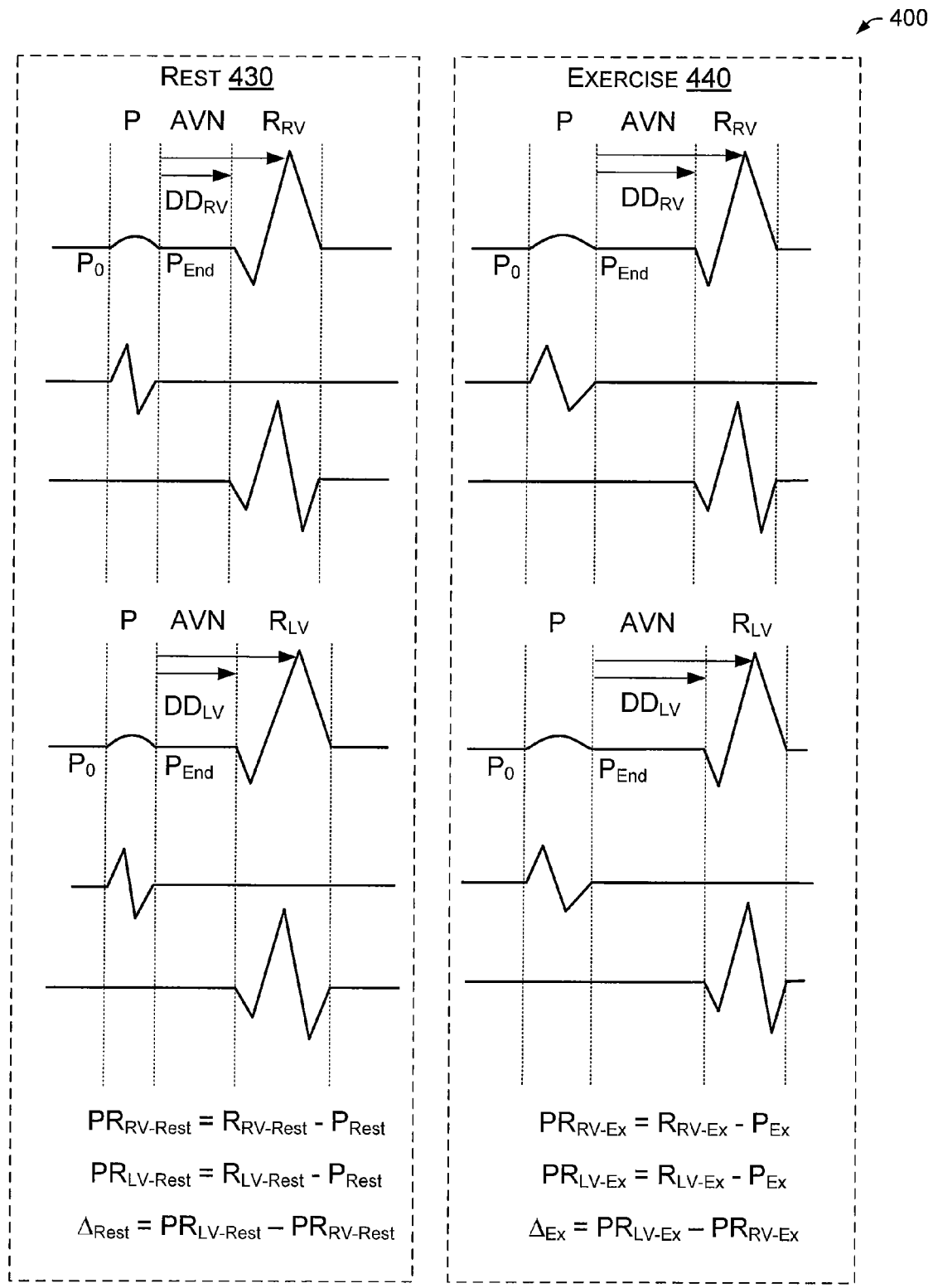
FIG. 4 is a set of rest state electrograms and a set of exercise state electrograms that exhibit various parameters.

FIG. 4 shows a series of electrograms that correspond to a rest state 430 and a series of electrograms that correspond to an active, exercise state 440. The electrograms 430, 440 include various labels as described with respect to the electrograms 310, 320 of FIG. 3 as well as labels for beginning of the P wave ($P_0$) and end of the P wave ($P_{End}$), where the duration of the P wave or P wave width ($\Delta P$) is $P_{End}-P_0$, and labels for an interval (DD) between the end of the P wave ($P_{End}$) and the beginning of the R wave or the QRS complex, for example, as detected by a conventional algorithm or other suitable technique. An R wave detection technique may rely on a slope or other feature of an R wave and a time other than the "beginning" of an R wave may be used. In various examples, a DD interval may rely on a detection technique used for R wave detection. As a DD interval relies on detection of an R wave or a QRS complex, an atrial to ventricular conduction pathway should exist for at least one ventricle because for patients with atrial to ventricular conduction block of both ventricles (e.g., RBBB and LBBB), a meaningful DD interval may not exist. For such patients, measurement of A wave width or P wave width may occur and such values may be used along with activity information for any of a variety of purposes (e.g., cardiac condition, pacing optimization, etc.).

As already mentioned, a PR interval typically relies on detecting $P_0$, the beginning of a P wave. In contrast, the interval DD relies on detecting $P_{End}$, the end of a P wave or approximate end of a P wave. Hence, the PR interval is always less than the DD interval for a particular ventricle, noting that one ventricle may have a DD interval that exceeds a PR interval of the other ventricle.

In the example of FIG. 4, a comparison between the rest state electrograms 430 and the exercise state electrograms 440 indicates that the P wave duration ($\Delta P$) and the DD interval increase with increasing activity. Under normal circumstances, the PP interval and RR interval decreases with increasing activity, hence, the ratio of P wave duration and DD interval to PP interval or RR interval increases.

Other variables such as PR and $\Delta$ may also change with respect to activity. For example, the PR interval may increase where the increase depends on the points used to define the PR interval. However, with respect to $\Delta$, the change may be somewhat uncertain, especially if little data exists for a patient or the patient's condition has changed.

As indicated in FIG. 4, a rest state $PR_{RV-Rest}$, $PR_{LV-Rest}$ and $\Delta_{Rest}$ may be determined as well as an exercise state $PR_{RV-Ex}$, $PR_{LV-Ex}$ and $\Delta_{Ex}$. These values may be used to adjust any of a variety of pacing parameters. Other values for use in adjusting one or more pacing parameters are discussed in more detail below.

While FIGS. 3 and 4 pertain to intrinsic atrial activity, FIG. 5 shows an approximate anatomical diagram of a heart and two sets of waveforms 500 pertaining to atrial pacing scenarios. One set of waveforms 510 corresponds in part to right ventricular activity while another set of waveforms 520 corresponds in part to left ventricular activity. Action potentials propagating through the heart are labeled as follows: 1, associated with a paced atrial stimulus and the atria; 2, associated with the atrio-ventricular node (AVN); and 3, associated with right and left bundle branches of the ventricles. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

The two sets of waveforms 510, 520 show heart activity (e.g., polarization, depolarization, etc.) wherein atrial depolarization is represented as an "A wave" and ventricular depolarization is represented as an "R wave", or QRS complex. Both sets 510, 520 show an A wave followed by an AVN conduction delay (AVN) and a right ventricular R wave or QRS complex ($R_{RV}$) for the set 510 and a left ventricular R wave or QRS complex ($R_{LV}$) for the set 520. Often detection of an R wave or QRS complex relies on signal amplitude or signal derivative with respect to time. Further, many detection methods are capable of assigning a time to a detected R wave or QRS complex or assigning a time span to an A wave to R wave or QRS complex interval, which are shown in FIG. 5 as $AR_{RV}$ for the right ventricle and $AR_{LV}$ for the left ventricle. If $AR_{RV}$ and $AR_{LV}$ are approximately equal, then the right ventricle and the left ventricle contract in an approximately synchronous manner. However, if $AR_{RV}$ and $AR_{LV}$ differ substantially, e.g., $|\Delta|=|AR_{LV}-AR_{RV}|>5$ ms, then the right ventricle and left ventricle contract in an asynchronous manner. Depending on patient or other factors, the time could be set at some time other than 5 ms. The variable $|\Delta|$ is shown as the absolute value of the difference while herein and in the figures the variable $\Delta$ (e.g., $\Delta=AR_{LV}-AR_{RV}$) may be less than zero when $AR_{RV}$ exceeds $AR_{LV}$ or greater than zero when $AR_{LV}$ exceeds $AR_{RV}$.

To facilitate measurement of $AR_{RV}$ or $AR_{LV}$, in instances where ventricular pacing occurs, the AV delay (e.g., $AV_{RV}$ and/or $AV_{LV}$) may be increased to a value greater than the expected $AR_{RV}$ or $AR_{LV}$. Of course, where possible, ventricular pacing is optionally disabled, set to a back-up mode, etc.

The electrograms 510, 520 of FIG. 5 include labels for beginning of the A wave ($A_0$) and end of the A wave ($A_{End}$), where the duration of the A wave or A wave width ($\Delta A$) is $A_{End}-A_0$, and labels for an interval (AD) between the end of the A wave ($A_{End}$) and the beginning of the R wave or the QRS complex, for example, as detected by a conventional algorithm or other suitable technique. The beginning of the A wave ($A_0$) is typically known by a pacing device, however, another device may include circuitry to sense or detect A wave characteristics (e.g., $A_0$, $A_{End}$, etc.) or acquire such information from a pacing device.

As in the example of FIG. 4, a comparison between rest state electrograms and exercise state electrograms, where atrial pacing occurs, may be expected to indicate similar trends in that the A wave duration ($\Delta A$) and the AD interval increase with increasing activity. Under normal circumstances, while the AA interval is controlled (e.g., set to a constant or adjusted with respect to activity or other variable), the ratio of A wave duration and AD interval to AA interval or RR interval may be expected to increase.

Other variables such as AR and $\Delta$ may also change with respect to activity. For example, the AR interval may increase where the increase depends on the points used to define the AR interval. However, with respect to A, the change may be somewhat uncertain, especially if little data exists for a patient or the patient's condition has changed.

As with respect to intrinsic atrial activity, for paced atrial activity, a rest state $AR_{RV-Rest}$, $AR_{LV-Rest}$ and $\Delta_{Rest}$ may be determined as well as an exercise state $AR_{RV-Ex}$, $AR_{LV-Ex}$ and $\Delta_{Ex}$. These values may be used to adjust any of a variety of pacing parameters. Other values for use in adjusting one or more pacing parameters are discussed in more detail below.

Figure 6:
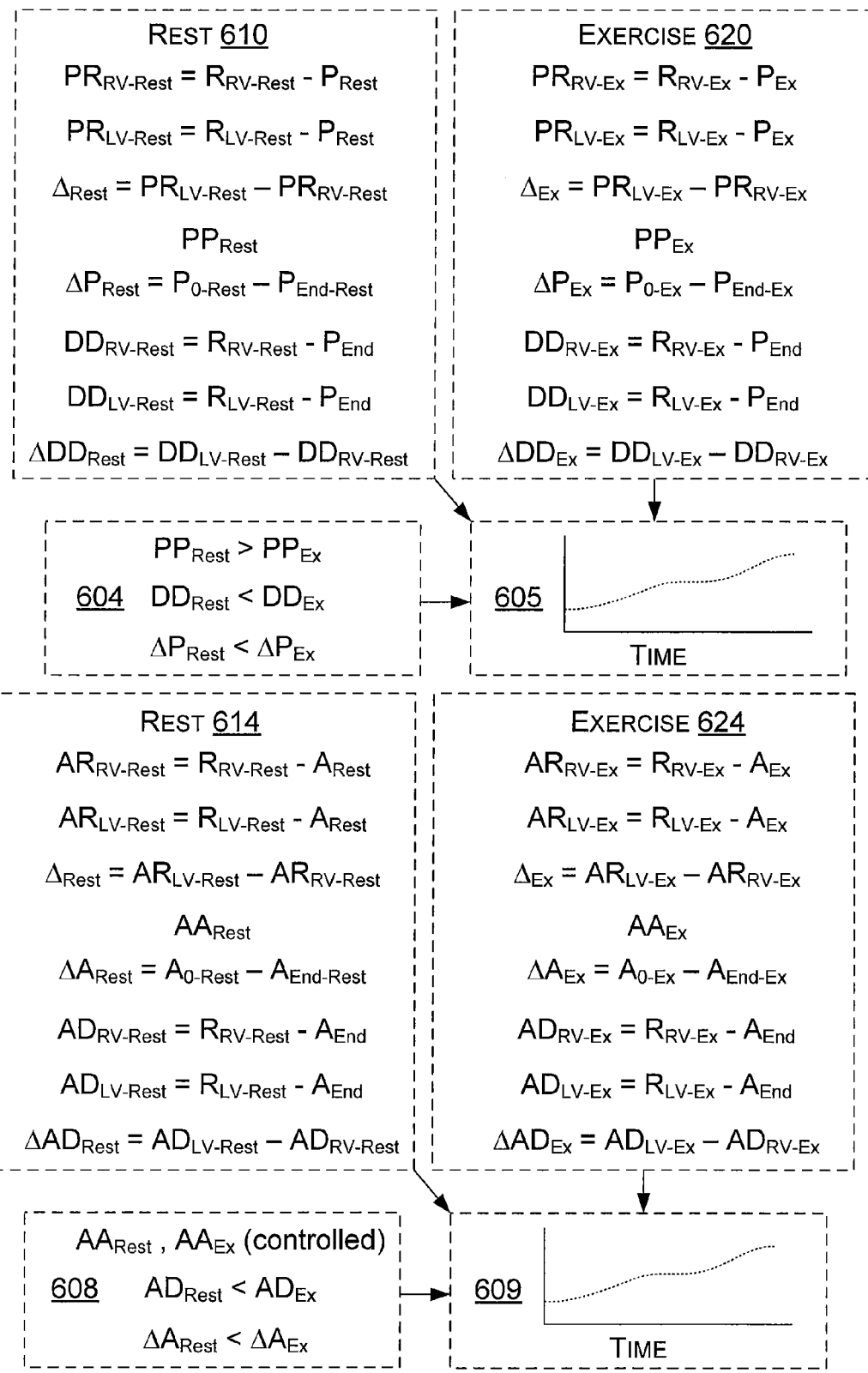
FIG. 6 is a series of equations and relationships for rest states and exercise or active states that may be used to determine one or more pacing parameters.

FIG. 6 shows various equations for rest state 610 and exercise state 620 for intrinsic and rest state 614 and exercise state 624 for paced atrial activation. For intrinsic atrial activation, relationships 604 indicate that $PP_{Rest}<PP_{Ex}$, $DD_{Rest}<DD_{Ex}$ and $\Delta P_{Rest}<\Delta P_{Ex}$ while for paced atrial activation, relationships 608 indicate that $AA_{Rest}$ and $AA_{Ex}$ are controlled, $AD_{Rest}<AD_{Ex}$ and $\Delta A_{Rest}<\Delta A_{Ex}$. Other variables include $\Delta DD_{Rest}$, $\Delta DD_{Ex}$, $\Delta AD_{Rest}$ and $\Delta AD_{Ex}$.

Plots 605, 609 are associated with intrinsic atrial activation and paced atrial activation, respectively, and indicate that various parameter values may be stored over time. Changes in value may indicate a change in cardiac condition. An analysis may compare a rest state value to an active state value. For example, an analysis may calculate a difference $\Delta_{Rest-Ex}$ as $DD_{Rest}-DD_{Ex}$ where a $\Delta_{Rest-Ex}$ value less than zero indicates an abnormal cardiac condition. A comparison may use a threshold value to decide whether cardiac condition is normal, abnormal and/or to call for appropriate action.

An analysis may compare an intrinsic atrial activation value with a paced atrial activation value. Such analyses may be used to assess cardiac condition. An exemplary method may periodically call for measurement of one or more parameter values or call for such measurement responsive to occurrence of an event or condition.

Referring to FIG. 7, an approximate anatomical diagram of a heart and two sets of waveforms 700 for ventricular pacing are shown. One set of waveforms 710 corresponds to atrial and right ventricular activity and the other set of waveforms 720 corresponds to atrial and left ventricular activity. The two sets of waveforms approximate IEGM waveforms that may be sensed in vivo using an implanted device. In both sets 710, 720, A represents an atrial waveform based on an atrial pace and ER represents an evoked response (e.g., capture) based on a ventricular pace (labeled "$V_{RV}$" or "$V_{LV}$").

In FIG. 7, action potentials propagating through the heart are labeled as follows: 1, associated with a paced atrial stimulus or an intrinsic SAN stimulus and the atria; 2, associated with the atrio-ventricular node (AVN); and 3, associated with a paced right ventricle and a paced left ventricle. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3). However, ventricular pacing may override an atrial paced or intrinsic stimulus or may allow for ventricular stimulation and contraction where AVN conduction is impaired. Thus, in this example, ventricular rhythm typically relies on ventricular stimulation and conduction of electrical activity through the ventricles.

As mentioned, the two sets of waveforms of heart activity (e.g., polarization, depolarization, etc.) include atrial depolarization represented as an "A wave" and ventricular depolarization represented as an "ER wave" or evoked response. The delay between the atrial stimulus and the right ventricular stimulus is referred to as $AV_{RV}$ while the delay between the atrial stimulus and the left ventricular stimulus is referred to as $AV_{LV}$. The set 710 shows an A wave followed by an AVN conduction delay (AVN) and a right ventricular ER wave or evoked response. The set 720 shows an A wave followed by an AVN conduction delay (AVN) and a left ventricular evoked response ($ER_{LV}$). Often detection of an R wave or an evoked response relies on signal amplitude or signal derivative with respect to time. Further, many detection methods are capable of assigning a time to a detected R wave or evoked response or assigning a time span to an A wave to R wave or evoked response interval, which are shown in FIG. 7 as A-$ER_{RV}$ for the right ventricle and A-$ER_{LV}$ for the left ventricle. If A-$ER_{RV}$ and A-$ER_{LV}$ are approximately equal, then the right ventricle and the left ventricle contract in a substantially synchronous manner. While FIG. 7 shows a paced atrial stimulus, an intrinsic SAN stimulus may suffice and hence result in P-ER waveforms and corresponding P-$ER_{RV}$ and P-$ER_V$ times. Where pacing occurs in both ventricles, corresponding IEGM waveforms may appear substantially the same as those of the set 710 and/or the set 720. Noting that, in general, an implanted device typically has a single atrial sensing channel and typically one or two ventricular channels (e.g., optionally one switchable channel that can switch between sensing in the left ventricle and the right ventricles and/or one ventricle and both ventricles).

As described herein, an exemplary method may program a $\Delta$ interval based at least in part on activity or an indicator of activity where $\Delta_{programmed}=AV_{LV}-AV_{RV}$ or $PV_{LV}-PV_{RV}$, where one ventricle optionally relies on a conducted event for ventricular activation (e.g., $R_{LV}$ or $R_{RV}$). For bi-ventricular pacing, a $\Delta_{programmed}$ value less than zero indicates that a pacing stimulus or stimuli was delivered to the left ventricle prior to the right ventricle. A $\Delta_{programmed}$ of zero indicates that both $AV_{RV}$ and $AV_{LV}$ or $PV_{RV}$ and $PV_{LV}$ were set to approximately equal AV or PV times, which may optionally be an overall optimal time (e.g., $AV_{optimal}$ and $PV_{optimal}$).

An exemplary method may acquire an echocardiogram, for example, to determine a velocity time integral, VTI, which is the product of blood velocity in the aorta over a period of time. In general, the period of time corresponds to a beat-to-beat time and hence VTI typically correlates well with or serves as an indicator of cardiac performance. Thus, a higher VTI value normally indicates better cardiac performance. For many patients, cardiac performance is improved by pacing the left ventricle prior to the right ventricle. For any particular patient, an optimal $\Delta_{programmed}$ may exist, which is referred to herein as $\Delta_{optimal}$.

A comparison between $\Delta$ and $\Delta_{programmed}$ or $\Delta_{optimal}$ can indicate a difference between a current cardiac therapy or state and a potentially better cardiac therapy or state. For example, consider the following equation (Eqn. 1):

$$\alpha = \Delta_{optimal}/\Delta \qquad (1)$$

where $\alpha$ is an optimization parameter. Various echocardiogram studies indicate that the parameter a is typically about 0.5. The use of such an optimization parameter is described further below, noting that such a parameter is optional for some techniques. In general, the closer $\alpha$ is to unity, there may be little need to pace either ventricle if the $PR_{RV}$, $PR_{LV}$, $AR_{RV}$, and/or $AR_{LV}$ times are acceptable (noting that acceptable AR times are generally longer than acceptable PR times due to conduction differences between a paced atrial stimulus and intrinsic atrial activity).

Another delay time, $\Delta_{IVCD}$, referred to an interventricular conduction delay (IVCD), which may be a paced interventricular conduction delay (PIVCD) or an interventricular conduction delay based at least in part on conducted activation. A PIVCD may be determined by pacing in a right ventricle and sensing in a left ventricle wherein the time between pacing and sensing is referred to as a right to left PIVCD or PIVCD-RL, which equals $R_{LV}-V_{RV}$, wherein $V_{RV}$ is a pace time of a pacing stimulus in the right ventricle and $R_{LV}$ is a sense time of a right ventricle, evoked response wavefront in the left ventricle due to the paced stimulus in the right ventricle. Thus, PIVCD-RL is normally greater than zero. To ensure that the pacing stimulus in the right ventricle results in an evoked response, a capture routine or algorithm may be implemented. Thus, various exemplary methods, devices and/or systems include a capture algorithm (e.g., autocapture).

When determining a PIVCD-RL or PIVCD-LR, to ensure that the sensed evoked response in the left ventricle $R_{LV}$ is not due to conducted electrical activity from the atria, a sufficiently short ventricular paced delay $AV_{RV}$ may be used. For example, a paced delay $AV_{RV}$ of approximately 30 ms to approximately 70 ms may suffice. In one example, $AV_{RV}$ is set to approximately 50 ms to approximately 80 ms. $AV_{RV}$ may also be set sufficiently short to avoid fusion. While AV is referred to, PV may also apply where appropriate.

In general, bipolar sensing (or other multipolar/combipolar sensing) may increase signal to noise of the sensed activation in the left ventricle when compared to unipolar sensing that includes use of an in vivo, yet non-local electrode such as a pulse generator can. The latter technique is more often used in detection of evoked response or applications utilizing far-field signals. Further, bipolar sensing that includes two electrodes positioned in proximity to each other (e.g., less than approximately 4 cm), may increase signal to noise and sensitivity and better sense timing of an activation wave front proximate to the electrodes.

Thus, in summary, FIG. 3 through FIG. 7 described the following delays that are related to pacing in the right ventricle and/or the left ventricle:

PP, AA Interval between successive atrial events
PV Delay between an atrial event and a paced ventricular event
$PV_{optimal}$ Optimal PV delay
$PV_{RV}$ PV delay for right ventricle
$PV_{LV}$ PV delay for left ventricle
AV Delay for a paced atrial event and a paced ventricular event
$AV_{optimal}$ Optimal AV delay
$AV_{RV}$ AV delay for right ventricle
$AV_{IV}$ AV delay for left ventricle
$\Delta$ Estimated interventricular delay, e.g., via IEGM, etc.
$\Delta_{programmed}$ Programmed interventricular delay (e.g., a programmed W delay)
$\Delta_{optimal}$ Optimal interventricular delay, e.g., via hemodynamic sensing/sensor or other cardiac sensing
IVCD-RL Delay between an RV event and a consequent sensed LV event
IVCD-LR Delay between an LV event and a consequent sensed RV event
$\Delta_{IVCD}$ Interventricular conduction delay
$\Delta P$, $\Delta A$ Width of an atrial event
DD, AD Interval between end of an atrial wave (e.g., P or A wave) and beginning of a R or QRS complex or other appropriate point
$\Delta DD$, $\Delta AD$ $DD_{LV}-DD_{RV}$ or $AD_{LV}-AD_{RV}$ Various scenarios are possible where delay information includes a delay between an atrial event (e.g., A or P) and a sensed ventricular event (e.g., R). In a first scenario, Scenario I, delay information, $AR_{LV}$ and/or $AR_{RV}$ (or $PR_{LV}$ and/or $PR_{RV}$), is assessed relative to a predetermined delay, $AR_{max}$ (or $PR_{max}$). As already mentioned, $AR_{max}$ or $PR_{max}$ may be approximately 250 ms or approximately 200 ms, respectively. Other values may be suitable depending on patient or other circumstances. In Scenario I, if one of the delays exceeds the predetermined delay, then pacing should occur in the ventricle associated with the delay that exceeds the predetermined delay. This ventricle is referred to herein as the master ventricle. For example, if $AR_{max}$ is 250 ms, $AR_{RV}$ is 150 ms and $AR_{LV}$ is 300 ms, then pacing should occur in the left ventricle because $AR_{LV}$ is greater than 250 ms.

In a second scenario, Scenario II, delay information, $AR_{LV}$ and $AR_{RV}$ (or $PR_{LV}$ and $PR_{RV}$), is assessed relative to a predetermined delay, $AR_{max}$ (or $PR_{max}$). In Scenario II, if both of the delays exceed the predetermined delay, then pacing should occur in both ventricles and first in the ventricle associated with the longest delay, which ventricle is referred to herein as the master ventricle. For example, if $PR_{max}$ is 200 ms, $PR_{RV}$ is 250 ms and $PR_{LV}$ is 300 ms, then pacing should occur both ventricles and first in the left ventricle because $PR_{LV}$ is greater than $PR_{RV}$.

In a third scenario, Scenario III, delay information, $AR_{LV}$ and $AR_{RV}$ (or $PR_{LV}$ and $PR_{RV}$), is assessed relative to a predetermined delay, $AR_{max}$ (or $PR_{max}$). In Scenario III, if both of the delays do not exceed the predetermined delay, then ventricular pacing may or may not occur depending on one or more other circumstances. For example, if $AR_{max}$ is 250 ms, $AR_{RV}$ is 150 ms and $AR_{LV}$ is 200 ms, then pacing may not occur because intrinsic conduction is apparently adequate. However, if the difference between $AR_{RV}$ and $AR_{LV}$ is deemed excessive or otherwise undesirable, then single or bi-ventricular pacing may occur in an effort to compensate or correct for this difference.

A scenario may use interventricular conduction delay (IVCD) information, for example, a delay between a paced event (e.g., V) in one ventricle and a sensed event (e.g., R) in the other ventricle or a delay between a conducted event in one ventricle and a consequential event in the other ventricle (e.g., where a block exists for one ventricle, etc.). Thus, such delay information pertains to conduction between the right ventricle and the left ventricle.

Various examples rely on a comparison between $|\Delta_{IVCD}|$ and an IVCD conduction related parameter $\epsilon$. The parameter $\epsilon$ represents an interventricular conduction limit for conduction between the ventricles and may represent a tolerable limit for conduction heterogeneity. For example, a large may be used to tolerate or to not compensate for conduction in one direction being significantly greater than conduction in the other direction.

If $AR_{LV}$ is greater than $AR_{max}$ (or $PR_{LV}$ is greater than $PR_{max}$) and $|\Delta_{IVCD}|$ is less than E, then pacing occurs in the left ventricle wherein the timing of the paced stimulus (or stimuli) follows the equation (Eqn. 2):

$$AV_{LV}=AV_{optimal}-|\Delta| \text{ or } PV_{LV}=PV_{optimal}-|\Delta| \quad (2)$$

In Eqn. 2, $AV_{optimal}$ or $PV_{optimal}$ represents an optimal or predetermined delay. Thus, Eqn. 2 ensures that pacing compensates for at least some of the conduction problem associated with the left ventricle. If however, $|\Delta_{IVCD}|$ is greater than or equal to $\epsilon$, then pacing occurs in the left ventricle wherein the timing of the paced stimulus (or stimuli) follows the equation (Eqn. 3):

$$AV_{LV}=AV_{optimal}-(|\Delta|+\Delta_{IVCD}) \text{ or }$$

$$PV_{LV}=PV_{optimal}-(|\Delta|+\Delta_{IVCD}) \quad (3)$$

Thus, Eqn. 3 ensures that pacing compensates for at least some of the conduction problem associated with the left ventricle and for at least some of the conduction problem associated with conduction between ventricles.

Consider a situation where $AR_{max}$ is 250 ms, $AR_{LV}$ is 300 ms, $AR_{RV}$ is 210 ms, $AV_{optimal}$ is 180 ms, $\epsilon$ is 5 ms, PIVCD-LR is 10 ms and PIVCD-RL is 20 ms (better left to right or poorer right to left conduction). In this situation, $|\Delta|$ is |300 ms−210 ms| or 90 ms and $\Delta_{PIVCD}$ is (10 ms−20 ms) or −10 ms. Thus, pacing should occur in the left ventricle with an atrio-ventricular delay as follows:

$$AV_{LV}=180 \text{ ms}-(90 \text{ ms}+(-10 \text{ ms}))=100 \text{ ms}$$

In this example, if $AR_{RV}$ is 210 ms, then the difference between ventricular activation is approximately 210 ms−100 ms or 110 ms, wherein the left ventricle is activated prior to the right ventricle, which may be referred to as $|\Delta_{actual}|$ which is equal to $|AV_{LV}-AR_{RV}|$.

If $AR_{RV}$ is greater than $AR_{max}$ (or $PR_{RV}$ is greater than $PR_{max}$) and $|\Delta_{IVCD}|$ is less than $\epsilon$, then pacing occurs in the right ventricle wherein the timing of the paced stimulus (or stimuli) follows the equation (Eqn. 4):

$$AV_{RV}=AV_{optimal}-|\Delta| \text{ or } PV_{Rv}=PV_{optimal}-|\Delta| \quad (4)$$

In Eqn. 4, $AV_{optimal}$ or $PV_{optimal}$ represents an optimal or predetermined delay. Thus, Eqn. 4 ensures that pacing compensates for at least some of the conduction problem associated with the right ventricle. If however, $|\Delta_{IVCD}|$ is greater than or equal to $\epsilon$, then pacing occurs in the right ventricle wherein the timing of the paced stimulus (or stimuli) follows the equation (Eqn. 5):

$$AV_{RV}=AV_{optimal}-(|\Delta|-\Delta_{IVCD}) \text{ or }$$

$$PV_{RV}=PV_{optimal}-(|\Delta|-\Delta_{IVCD}) \quad (5)$$

Thus, Eqn. 5 ensures that pacing compensates for at least some of the conduction problem associated with the right ventricle and for at least some of the conduction problem associated with conduction between ventricles.

Consider a situation where $AR_{max}$ is 250 ms, $AR_{RV}$ is 280 ms, $AR_{LV}$ is 230 ms, $AV_{optimal}$ is 190 ms, E is 5 ms, PIVCD-LR is 10 ms and PIVCD-RL is 20 ms (better left to right or poorer right to left conduction). In this situation, $|\Delta|$ is |230 ms−280 ms| or 50 ms and $\Delta_{IVCD}$ is (10 ms−20 ms) or −10 ms. Thus, pacing should occur in the right ventricle with an atrio-ventricular delay as follows:

$$AV_{RV}=190 \text{ ms}-(50 \text{ ms}-(-10 \text{ ms}))=130 \text{ ms}$$

In this situation, the calculated delay of the pacing stimulus (or stimuli) in the right ventricle accounts for conduction issues from the atria to the ventricles and for poor right to left interventricular conduction. Further in this example, if $AR_{LV}$ is 230 ms, then the difference between ventricular activation is approximately 230 ms−130 ms or 100 ms, wherein the right ventricle is activated prior to the left ventricle, which may be referred to as $|\Delta_{actual}|$ which is equal to $|AR_{LV}-AV_{RV}|$.

In other examples for Scenario II, at least some delay information is known about interventricular conduction delay (IVCD). In these scenarios, such delay information may pertain to delay between a paced event (e.g., V) in one ventricle and a sensed event (e.g., R) in the other ventricle or a conducted event in one ventricle that causes a response in the other ventricle. Regardless of the nature of the interventricular conduction delay, such delay information pertains to conduction between the right ventricle and the left ventricle.

A more specific example relies on a comparison between $|\Delta_{IVCD}|$ and an IVCD conduction related parameter $\epsilon$. The parameter $\epsilon$ represents an interventricular conduction limit for conduction between the ventricles and may represent a tolerable limit for conduction heterogeneity. For example, a large $\epsilon$ may be used to tolerate or to not compensate for conduction in one direction being significantly greater than conduction in the other direction.

If $AR_{LV}$ and $AR_{RV}$ are greater than $AR_{max}$ (or $PR_{LV}$ and $PR_{RV}$ are greater than $PR_{max}$), $AR_{LV}$ is greater than $AR_{RV}$ and $|\Delta_{IVCD}|$ is less than $\epsilon$, then pacing occurs in both ventricles where $AV_{RV}$ is set to $AV_{optimal}$ and in the left ventricle the timing of the paced stimulus (or stimuli) follows the equation (Eqn. 6):

$$AV_{LV}=AV_{RV}-|\Delta| \text{ or } PV_{LV}=PV_{RV}-|\Delta| \quad (6)$$

Thus, Eqn. 6 ensures that pacing compensates for at least some of the conduction problem associated with the left ventricle. If however, $|\Delta_{IVCD}|$ is greater than or equal to $\epsilon$, then $AV_{RV}$ is set to $AV_{optimal}$ and pacing occurs in the left ventricle wherein the timing of the paced stimulus (or stimuli) follows the equation (Eqn. 7):

$$AV_{LV}=AV_{RV}-(|\Delta|+\Delta_{PIVCD}) \text{ or }$$

$$PV_{LV}=PV_{RV}-(|\Delta|+\Delta_{PIVCD}) \quad (7)$$

Thus, Eqn. 7 ensures that pacing compensates for at least some of the conduction problem associated with the left ventricle and for at least some of the conduction problem associated with conduction between ventricles.

Consider a situation where $AR_{max}$ is 250 ms, $AR_{LV}$ is 300 ms, $AR_{RV}$ is 260 ms, $AV_{optimal}$ is 180 ms, $\epsilon$ is 5 ms, PIVCD-LR is 10 ms and PIVCD-RL is 20 ms (better left to right or poorer right to left conduction). In this situation, $|\Delta|$ is |300 ms–260 ms| or 40 ms and $\Delta_{IVCD}$ is (10 ms–20 ms) or –10 ms. Thus, pacing should occur in the left ventricle with an atrio-ventricular delay as follows:

$$AV_{LV}=180 \text{ ms}-(40 \text{ ms}+(-10 \text{ ms}))=150 \text{ ms}$$

In this example, if $AV_{RV}$ is 180 ms, then the difference between ventricular activation is approximately 180 ms–150 ms or 30 ms, wherein the left ventricle is activated prior to the right ventricle, which may be referred to as $\Delta_{actual}$ which is equal to $|AV_{LV}-AV_{RV}|$.

If $AR_{RV}$ and $AR_{LV}$ are greater than $AR_{max}$ (or $PR_{RV}$ and $PR_{LV}$ are greater than $PR_{max}$), $AR_{RV}$ is greater than $AR_{LV}$ and $|\Delta_{IVCD}|$ is less than $\epsilon$, then $AV_{LV}$ is set to $AV_{optimal}$ and pacing occurs in the right ventricle wherein the timing of the paced stimulus (or stimuli) follows the equation (Eqn. 8):

$$AV_{RV}=AV_{LV}-|\Delta| \text{ or } PV_{RV}=PV_{LV}-|\Delta| \quad (8)$$

Thus, Eqn. 8 ensures that pacing compensates for at least some of the conduction problem associated with the right ventricle. If however, $|\Delta_{IVCD}|$ is greater than or equal to $\epsilon$, then $AV_{LV}$ is set to $AV_{optimal}$ and pacing occurs in the right ventricle wherein the timing of the paced stimulus (or stimuli) follows the equation (Eqn. 9):

$$AV_{RV}=AV_{LV}-(|\Delta|-\Delta_{IVCD}) \text{ or}$$

$$PV_{RV}=PV_{LV}-(|\Delta|-\Delta_{IVCD}) \quad (9)$$

Thus, Eqn. 9 ensures that pacing compensates for at least some of the conduction problem associated with the right ventricle and for at least some of the conduction problem associated with conduction between ventricles.

Consider a situation where $AR_{max}$ is 250 ms, $AR_{RV}$ is 280 ms, $AR_{LV}$ is 270 ms, $AV_{optimal}$ is 190 ms, $\epsilon$ is 5 ms, PIVCD-LR is 10 ms and PIVCD-RL is 20 ms (better left to right or poorer right to left conduction). In this situation, $|\Delta|$ is |1270 ms–280 ms| or 10 ms and $\Delta_{IVCD}$ is (10 ms–20 ms) or –10 ms. Thus, pacing should occur in the right ventricle with an atrio-ventricular delay as follows:

$$AV_{RV}=190 \text{ ms}-(10 \text{ ms}-(-10 \text{ ms}))=170 \text{ ms}$$

In this situation, the calculated delay of the pacing stimulus (or stimuli) in the right ventricle accounts for conduction issues from the atria to the ventricles and for poor right to left interventricular conduction. Further in this example, because $AV_{LV}$ is 190 ms, the difference between ventricular activation is approximately 190 ms–170 ms or 20 ms, wherein the right ventricle is activated prior to the left ventricle, which may be referred to as $|\Delta_{actual}|$ which is equal to $|AV_{LV}-AV_{RV}|$.

In the foregoing examples, there is no explicit compensation based on the parameter $\alpha$ (e.g., $\alpha=\Delta_{optimal}/\Delta$) as it does not appear in Eqns. 2 through 9. However, the parameter $\alpha$ may be used to further enhance cardiac performance in aforementioned Scenario I and/or Scenario II. An approach may use an optimal AV delay and use the parameter $\alpha$ to arrive at an optimal interventricular delay.

For $AR_{RV}>AR_{LV}$ (or $PR_{RV}>PR_{LV}$) and pacing in a single ventricle (e.g., Scenario I), the following equation (Eqn. 10) may be used to determine an appropriate $AV_{RV}$:

$$AV_{RV}=AV_{optimal}-\alpha|\Delta| \text{ or } PV_{RV}=PV_{optimal}-\alpha|\Delta| \quad (10)$$

In Eqn. 10 the term $\alpha|\Delta|$ equals or approximates $\Delta_{optimal}$. Thus, a patient's device may deliver therapy using an optimal atrio-ventricular delay in one chamber together with an optimal interventricular delay.

In instances where $\Delta_{IVCD}$ information is available and an adjustment for interventricular conduction desirable, then the following equation (Eqn. 11) may be used in Scenario I where $AR_{LV}>AR_{RV}$ (or $PR_{LV}>PR_{RV}$):

$$AV_{LV}=AV_{optimal}-\alpha(|\Delta|+\Delta_{IVCD}) \text{ or}$$

$$PV_{LV}=PV_{optimal}-\alpha(|\Delta|+\Delta_{IVCD}) \quad (11)$$

For Scenario I where $AR_{RV}>AR_{LV}$ (or $PR_{RV}>PR_{LV}$), the sign of the interventricular conduction delay time is switched from "+" to "–", where $\Delta_{IVCD}$ is defined as IVCD-LR–IVCD-RL. Similar equations exist for Scenario II, wherein the parameter $\alpha$ is used to adjust $\Delta$ or the term $|\Delta|+/-\Delta_{IVCD}$.

While the parameter $\alpha$ was described with respect to echocardiogram data, other techniques may be suitable to determine such a parameter. As already mentioned, the parameter $\alpha$ may depend on or be adjusted based wholly, or in part, on IEGM information acquired in vivo using traditional sensing leads, electrodes and circuitry. Further, a patient may have more than one such parameter. For example, a patient may have an $\alpha_{sleep}$ (and/or an $\alpha_{rest}$), an $\alpha_{exercise}$, an $\alpha_{normal}$, etc., depending on conditions or states the patient is likely to experience. In such a manner, a detector may detect a condition or state and then select a corresponding $\alpha$. Parameters and/or parameter selection may be based on cardiac information such as QRS and conduction times. For example, if a patient exhibits normal $PR_{RV}$, conduction, a QRS less than approximately 150 ms and excessive $PR_{LV}$ conduction, then $\alpha$ may be set to 0.5 or other value as appropriate. Various sensors are mentioned above with respect to the exemplary device 100 of FIG. 2. Such sensors may provide information for use in determining an $\alpha$ parameter or other parameters suitable for use in adjusting pacing variables.

Various information pertaining to conduction is optionally used to determine, estimate and/or update an optimal atrio-ventricular delay (e.g., $AV_{optimal}$ or $PV_{optimal}$). For example, if $AR_{RV}<AR_{RV}$ or $PR_{RV}<PR_{LV}$, a new optimal atrio-ventricular delay may be determined using the following equation (Eqn. 12):

$$AV_{optimal}(n+1)=AV_{optimal}(n)*(AR_{RV}(n+1)/AR_{RV}(n)) \text{ or}$$

$$AV_{optimal}(n+1)=AV_{optimal}(n)*(PR_{RV}(n+1)/PR_{RV}(n)) \quad (12)$$

If $AR_{LV}<AR_{RV}$ or $PR_{LV}<PR_{RV}$, then $AR_{LV}$ or $PR_{LV}$ could be used to update $AV_{optimal}$. For example, if $AR_{LV}(n+1)$ is 160 ms, $AR_{RV}(n+1)$ is 210 ms, $AV_{optimal}(n)$ is 150 ms and $AR_{LV}(n)$ is 170 ms, then $AV_{optimal}(n+1)$ is approximately 150 ms*(160 ms/170 ms) or 141 ms.

Updating of information such as an $AV_{optimal}$ delay may occur based on a schedule, a number of beats, a change in cardiac condition, etc. For example, if a change of more than 10% occurs in the shorter atrio-ventricular conduction delays over a 1 hour period, then $AV_{optimal}$ is updated. Of course, updating may occur upon a session with a caretaker wherein information is obtained and used to determine $AV_{optimal}$. Further, an exemplary implanted device optionally stores changes in $AV_{optimal}$ which may be subsequently used by a caretaker, for example, to improve therapy, to diagnose cardiac condition, etc.

Various exemplary methods described herein are optionally implemented using an implantable device having a single sensing channel for one or more electrodes positioned in or on the right ventricle and for one or more electrodes positioned in or on the left ventricle. In such devices, switching is optionally used to switch between sensing of the right ventricle and the left ventricle. Alternatively, both ventricles are sensed at the same time wherein an algorithm or other detection method is used to distinguish at least some information associated with the right ventricle from at least some information associated with the left ventricle.

An exemplary implantable device allows for acquisition of IEGMs using a unipolar sensing arrangement for a right ventricular tip electrode and a left ventricular tip electrode having a common electrode (e.g., can, device sensing circuit, etc.). In this unipolar arrangement, an electrical connection exists between right and left ventricular sensing circuits. In particular, depolarization due to atrio-ventricular intrinsic conduction was sensed at the right ventricle and then sensed at the left ventricle as the activation propagated to the left ventricle. In this example, the peak-to-peak time delay typically approximates Δ, however, it may approximate IVCD-RL. If RV is paced at a short AV delay, the time delay from pacing RV to the peak of the conduction to the left ventricle approximates IVCD-RL. In an alternative example, a pacing stimulus was delivered to the right ventricle at a time of approximately 0 ms. This pacing stimulus resulted in capture of the right ventricle and the IEGM showed a corresponding right ventricular evoked response. In this example, the left ventricle was not paced or initially captured by the pace to the right ventricle but after a short delay, the left ventricle depolarized spontaneously due to conduction of the paced event from the right ventricle. Hence, the delay between the right ventricular peak (RV) and the left ventricular peak (LV) approximates a paced interventricular conduction delay from right ventricle to left ventricle (e.g., IVCD-RL). Thus, an implantable device that uses a single sensing amplifier for right and left ventricular sensing channels may be used to determine interventricular conduction delay and thus, $\Delta_{IVCD}$. In addition, such a sensing arrangement may be used to determine a VV delay (e.g., Δ, etc.) based on an intrinsic or a paced atrial event that is then conducted to the left ventricle and the right ventricle.

Further, some implantable devices having sensing and pacing capabilities can deliver a stimulus to one ventricle and then switch to sensing of both ventricles. For example, a RV stimulus may be delivered in an open configuration (e.g., RV and LV leads/electrodes not "connected") and, thereafter, leads/electrodes "shorted" to allow for sensing from both ventricles. Of course, where appropriate, pacing in one ventricle and sensing in the other ventricle may occur according to various arrangements.

A ventricular IEGM was acquired in a study using an implantable device including switchable channel for RV and LV sensing. Such a device may allow for measurement of $AR_{RV}/PR_{RV}$ and $AR_{LV}/PR_{LV}$ by switching between RV sensing to LV sensing. Accordingly, Δ may be ascertained. Such a device may also allow for pacing in the right ventricle and/or left ventricle. Further, such a device may ascertain IVCD-RL and/or IVCD-LR and optionally $\Delta_{IVCD}$. For example, if an $AV_{RV}$ or $PV_{RV}$ delay is set short enough to avoid fusion, then $AR_{LV}$ or $PR_{LV}$ may be determined on the basis of LV sensing wherein the LV sensing sense electrical activity in the left ventricle (e.g., $R_{LV}$) stemming from the right ventricular stimulus (e.g., $V_{RV}$). In this example, IVCD-RL may equal $AR_{LV}-AV_{RV}$ or $PR_{LV}-PV_{RV}$.

Other implantable devices may include RV and LV sensing channels that can operate at the same time. Such devices may allow for measurement of $AR_{RV}/PR_{RV}$ and $AR_{LV}/PR_{LV}$ on a beat-by-beat basis. For example, for a single beat, an atrial to right ventricular delay and an atrial to left ventricular delay may be ascertained. Such an exemplary method can reduce measurement error by determining such variable for a single beat as compared to determining one variable for one beat and another variable for a different beat. Detection of an event may be based on sensitivity programmed in devices or a criterion such as an amplitude value greater than approximately 40% of an expected QRS amplitude value.

Various exemplary methods, devices and/or systems may help to avoid cross ventricular sensing. For example, if an interventricular delay is less than interventricular conduction (e.g., IVCD-RL and IVCD-LR), the incidence of sensing paced ventricular events in an alert interval is reduced. Further, this incidence may be further reduced through use of an automatic capture algorithm.

Various schemes exist for sensing an intrinsic or non-paced event for a single ventricular sensing channel. Where atrial information is required or desired (e.g., A wave or P wave information), an implantable device will generally include an atrial channel. An atrial channel may include an atrial pace blanking period, an alert period, a first ventricular blanking period (e.g., a master ventricle blanking period), a post ventricular atrial refractory period (PVARP), and a second ventricular blanking period (e.g., a slave ventricle blanking period). Some of these periods may be optional, depending, for example, on one or more sensed and/or programmed events.

With respect to a ventricular channel, such a channel may include an atrial blanking period, an alert period, a master ventricle pace event, a master ventricle blanking period, a ventricular refractory period (VRP, e.g., a master ventricle refractory period), and a second ventricular blanking period (e.g., a slave ventricle blanking period). Various events of a master ventricular channel will typically coincide or occur in coordination with one or more sensed and/or programmed events and/or periods of one or more other channels. Further, some of the events or periods of a ventricular channel may be optional depending, for example, on one or more sensed and/or programmed events.

Various implantable devices include more than one ventricular channel, where one may be assigned as a master ventricular channel and another as a slave ventricular channel. A slave ventricular channel may include an atrial blanking period, a first alert period, a master blanking period, a second alert period, a slave ventricle pace event, a slave ventricle blanking period, and a ventricular refractory period (VRP, e.g., a slave ventricle refractory period). Various events of the slave ventricular channel will typically coincide or occur in coordination with one or more sensed and/or programmed events and/or periods of one or more other channels. Further, some of the events or periods of a slave channel may be optional, depending, for example, on one or more sensed and/or programmed events.

Two particular cases exist for a slave channel that relate to detection or sensing of activity in the slave ventricle prior to delivery of a master ventricle pace event (e.g., Case I) and detection or sensing of activity in the slave ventricle after delivery of a master ventricle pace event (e.g., Case II). In Case I, the slave ventricle activity occurs in an alert period that lies somewhere between the atrial pace event (or detection/sensing of an intrinsic atrial event) and the scheduled delivery time of a master ventricle pace event. In response to Case I, an exemplary method, device, system, etc., may deliver a master ventricle pace and/or inhibit any scheduled slave ventricle pace. In delivering a pace to a master ventricle, an exemplary scheme may act via sensing or detecting to ensure that the pace avoids any vulnerable period (e.g., T wave, etc.). An alternative choice is also to inhibit the master channel. In Case II, the slave ventricle activity occurs in an alert period that lies somewhere between the master ventricle pace event and a scheduled slave ventricle pace event, for example, the alert period may be coextensive with a VV delay. In response to Case II, an exemplary method, device and/or system may inhibit the scheduled slave ventricle pace event.

A slave channel may indicate or include a master ventricle to slave ventricle conduction period (e.g., as determined by IVCD-RL, IVCD-LR, etc.). For example, a ventricular refractory period may extend to a time greater than the master ventricle to slave ventricle conduction period as measured from delivery of a master pace event. The refractory period may be represented by the following equation (Eqn. 13):

$$VRP_{Slave\ Ventricle} > IVCD\text{-}RL\ \text{or}\ IVCD\text{-}LR\text{-}VV \quad (13)$$

In Eqn. 13, the $VRP_{Slave\ Ventricle}$ follows the scheduled slave ventricle pace event.

Various schemes may help to avoid issues relating to double counting, which may trigger tachycardia therapy. For example, in some implantable devices, a pacing stimulus delivered to one ventricle may be sensed in the other ventricle and be classified as a fast ventricular rhythm (i.e., double counting). In an exemplary scheme, a desired VV delay is less than any inherent inter-ventricular conduction and thus, the probability of sensing ventricular paced beats in the alert interval is quite small. In addition, if an auto capture algorithm is used to detect capture of a paced stimulus; then, double counting may be avoided based on such detection.

Figure 8:
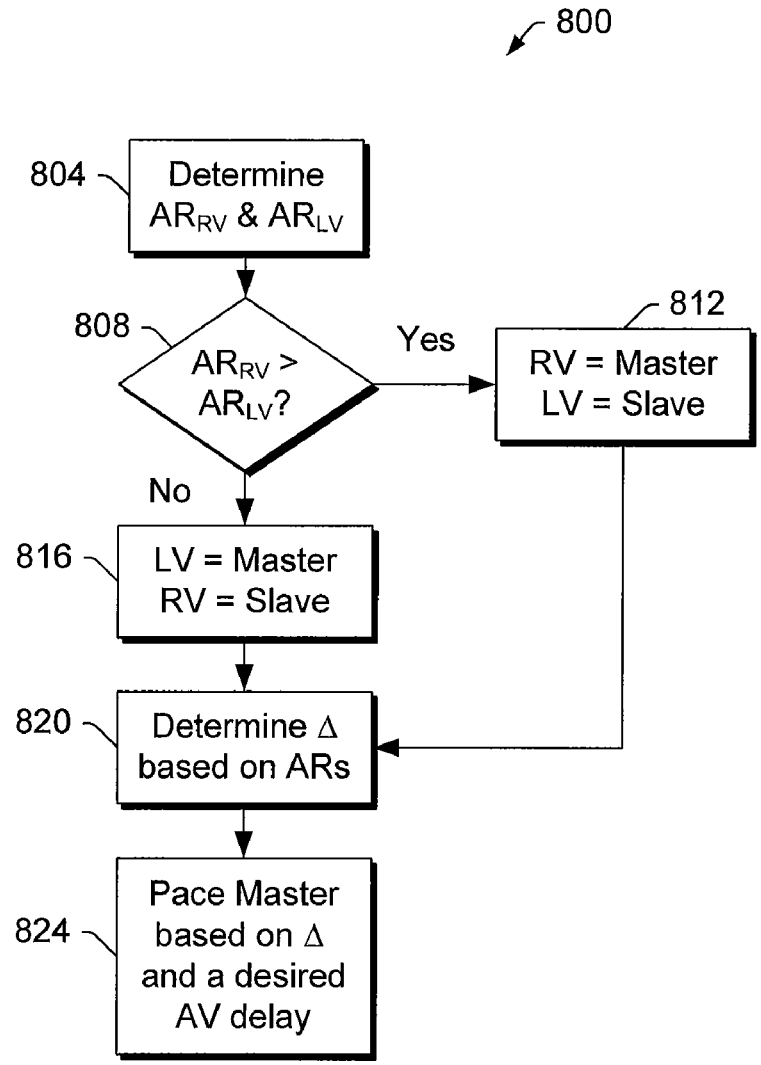
FIG. 8 is a block diagram of an exemplary method for ventricular pacing based on an $AR_{RV}$ time and an $AR_{LV}$ time.

FIG. 8 shows a block diagram of an exemplary method 800 for ventricular pacing. In a determination block 804, an implantable device determines an $AR_{RV}$ time and an $AR_{LV}$ time or equivalent times wherein one or both rely on detection of an intrinsic atrial event. A decision block 808 follows wherein a decision is made as to whether $AR_{RV}$ is greater than $AR_{LV}$. If $AR_{RV}$ exceeds $AR_{LV}$, then in a set block 812, the right ventricle is set to the master and the left ventricle is set to the slave. If $AR_{LV}$ exceeds $AR_{RV}$, then in a set block 816, the left ventricle is set to the master and the right ventricle is set to the slave. Both set blocks 812, 816 continue in a determination block 820 which determines a $\Delta$ value based on the $AR_{RV}$ and $AR_{LV}$ times. A pace master block 824 follows wherein the master ventricle is paced based on the $\Delta$ and a desired AV delay. The desired AV delay may be determined, for example, based on an echocardiogram or other study. The AV delay is optionally determined by an implantable device based on sensed information. Various techniques described further below use sensed information such as width of a P wave ($\Delta P$) or width of an A wave ($\Delta A$).

Thus, as described with respect to FIG. 8, such an exemplary method includes determining an atrial to ventricular activation time for a right ventricle, determining an atrial to ventricular activation time for a left ventricle, and determining a pacing sequence that paces the right ventricle prior to activation of the left ventricle if the time for the right ventricle exceeds the time for the left ventricle or that paces the left ventricle prior to activation of the right ventricle if the time for the left ventricle exceeds the time for the right ventricle wherein pacing of the prior activated ventricle occurs based at least in part on a difference between the time for the right ventricle and the time for the left ventricle and a desired atrio-ventricular delay. In some instances, an inter-ventricular delay may be used instead of, or in addition to, one or more atrial to ventricular activation times.

Figure 9:
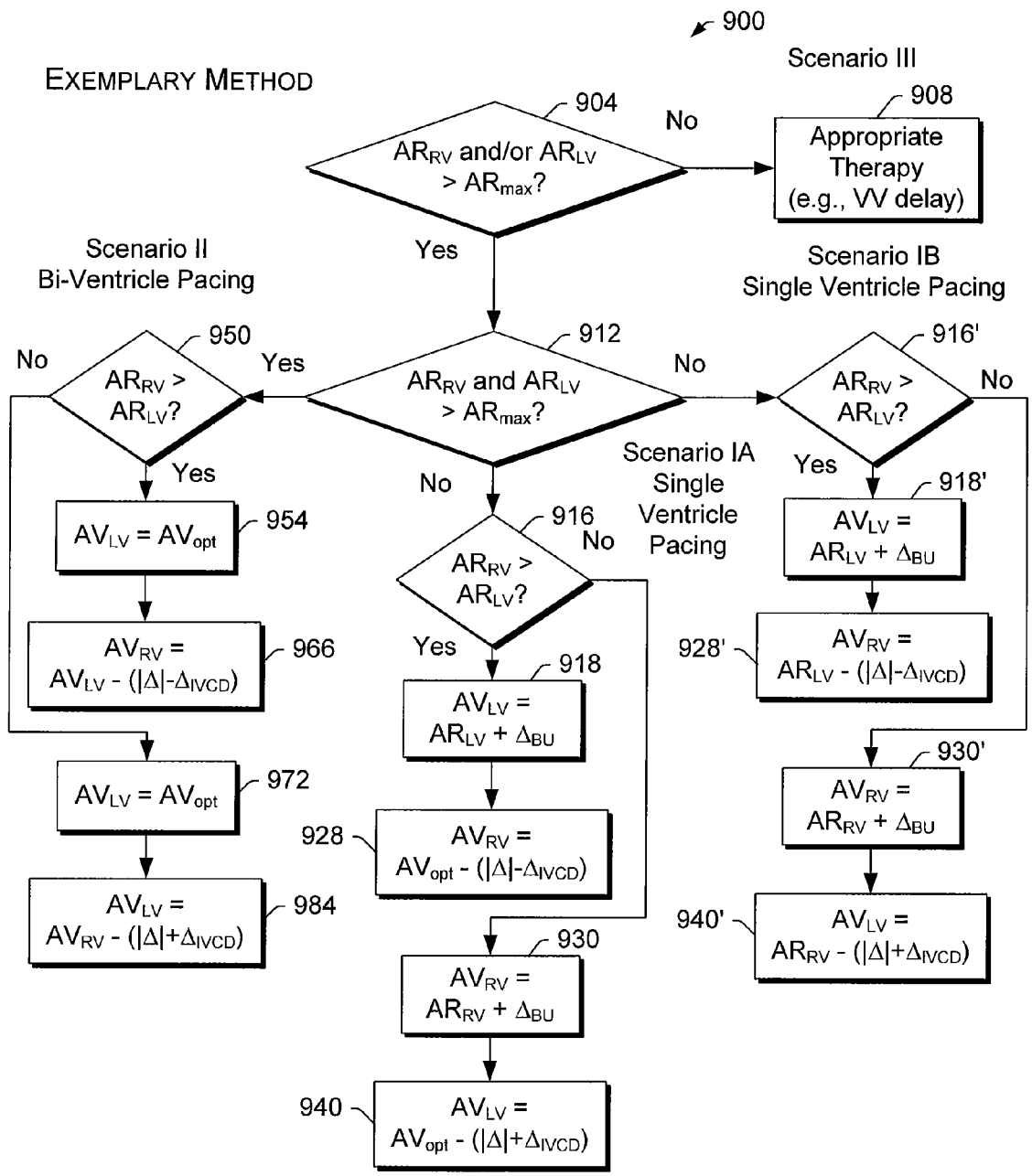
FIG. 9 is a block diagram of an exemplary method for ventricular pacing with scenarios for pacing a single ventricle and a scenario for pacing both ventricles.

FIG. 9 shows a block diagram of an exemplary method 900. While the method 900 pertains to atrial pacing, such a method may omit atrial pacing (e.g., rely on an intrinsic atrial activity, etc.) and/or include atrial pacing and intrinsic atrial activity, etc. (e.g., PR, AR, AV, and/or PV). The exemplary method 900 includes Scenarios IA, IB, II and III, where scenarios IA, II and III are generally as presented above. Other exemplary techniques are presented further below with respect to changes in activity, noting that activity-based techniques may be used for the method of FIG. 9.

In a decision block 904 a decision is made as to whether $AR_{RV}$ and/or $AR_{LV}$ have exceeded a predetermined $AR_{max}$ value. If neither value exceeds $AR_{max}$, then Scenario III follows, which may disable ventricular pacing or take other appropriate therapy per block 908. Other appropriate therapy optionally includes therapy that achieves a desirable VV delay by any of a variety of techniques. If however one or both values exceed $AR_{max}$, then the method 900 continues in another decision block 912. The decision block 912 decides whether $AR_{RV}$ and $AR_{LV}$ have exceeded $AR_{max}$. If both values do not exceed $AR_{max}$, then single ventricular pacing occurs, for example, per Scenario IA or Scenario IB. If both values exceed $AR_{max}$, then bi-ventricular pacing occurs, for example, Scenario II.

Scenario IA commences with a decision block 916 that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing per Scenario IA, the method 900 continues in a back-up pacing block 918 where $AV_{LV}$ is set to $AR_{LV}$ plus some back-up time (e.g., $\Delta_{BU}$). The block 918, while optional, acts to ensure that pacing will occur in the left ventricle if no activity occurs within some given interval. The method 900 then continues in a set block 928 where the parameter $\Delta_{IVCD}$ is used as a correction factor to set the $AV_{RV}$ delay to $AV_{optimal}-(|\Delta|-\Delta_{IVCD})$.

For left ventricular pacing per the Scenario IA, the method 900 continues in a back-up pacing block 930 where $AV_{LV}$ is set to $AR_{LV}$ plus some back-up time (e.g., $\Delta_{BU}$). The block 930, while optional, acts to ensure that pacing will occur in the left ventricle if no activity occurs within some given interval. The method 900 then continues in a set block 940 where the parameter $\Delta_{IVCD}$ is used as a correction factor to set the $AV_{LV}$ delay to $\Delta V_{optimal}-(|\Delta|+\Delta_{IVCD})$.

Scenario IB commences with a decision block 916' that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing per Scenario IB, the method 900 continues in a back-up pacing block 918' where $AV_{LV}$ is set to $AR_{LV}$ plus some back-up time (e.g., $\Delta_{BU}$). The block 918', while optional, acts to ensure that pacing will occur in the left ventricle if no activity occurs within some given interval. The method 900 then continues in a set block 928' where the parameter $\Delta_{IVCD}$ is used as a correction factor to set the $AV_{RV}$ delay to $AR_{LV}-(|\Delta|-\Delta_{IVCD})$. Hence, in this example, a pre-determined $AV_{optimal}$ is not necessary.

For left ventricular pacing per the Scenario IB, the method 900 continues in a back-up pacing block 930' where $AV_{LV}$ is set to $AR_{LV}$ plus some back-up time (e.g., $\Delta_{BU}$). The block 930', while optional, acts to ensure that pacing will occur in the left ventricle if no activity occurs within some given interval. The method 900 then continues in a set block 940' where the parameter $\Delta_{IVCD}$ is used as a correction factor to set the $AV_{LV}$ delay to $AR_{RV}-(|\Delta|+\Delta_{IVCD})$. Again, in this example, a pre-determined $AV_{optimal}$ is not necessary.

Referring again to the decision block 912, if this block decides that bi-ventricular pacing is appropriate, for example, Scenario II, then the method 900 continues in a decision block 950, which that decides if $AR_{RV}$ is greater than $AR_{LV}$. If $AR_{RV}$ exceeds $AR_{LV}$, then bi-ventricular pacing occurs wherein the right ventricle is the master (e.g., paced prior to the left ventricle or sometimes referred to as left ventricle slave). If $AR_{RV}$ does not exceed $AR_{LV}$, then bi-ventricular pacing occurs wherein the left ventricle is the master (e.g., paced prior to the right ventricle or sometimes referred to as right ventricle slave).

For right ventricular master pacing, the method 900 continues in a set block 954 which sets $AV_{LV}$ to $AV_{optimal}$. The method 900 then uses $\Delta_{IVCD}$ as a correction factor in a set block 966, which sets $AV_{RV}$ delay to $AV_{LV}-(|\Delta|-\Delta_{IVCD})$.

For left ventricular master pacing, the method 900 continues in a set block 972 which sets $AV_{RV}$ to $AV_{optimal}$. The method 900 then uses $\Delta_{IVCD}$ as a correction factor in a set block 984, which sets $AV_{LV}$ delay to $AV_{RV}-(|\Delta|+\Delta_{IVCD})$.

If a parameter such as the aforementioned α parameter is available, then such a parameter is optionally used to further adjust and/or set one or more delays, as appropriate (see, e.g., Eqns. 10 and 11).

Figure 10:
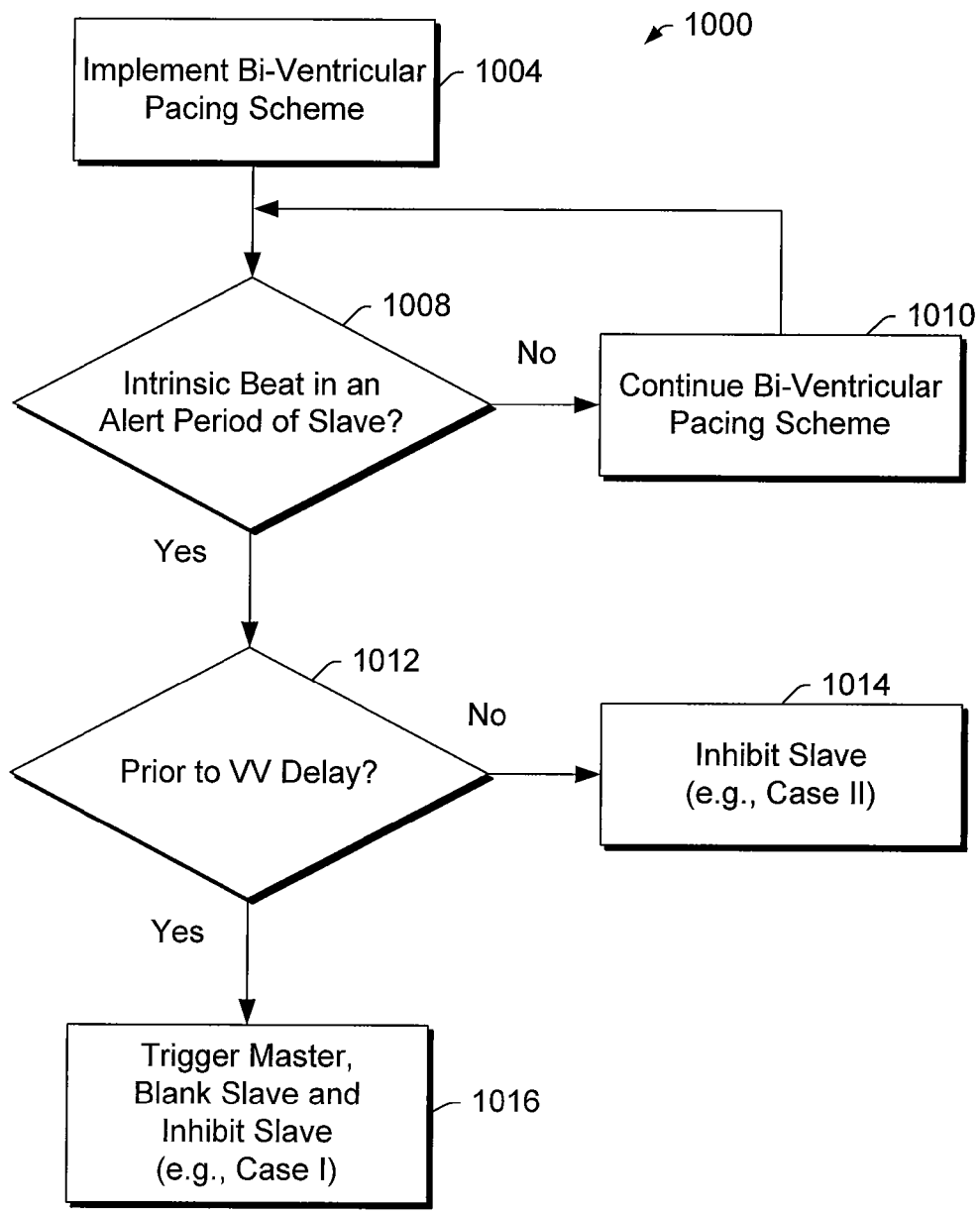
FIG. 10 is a block diagram of an exemplary method that includes immediate delivery of a master stimulation and/or inhibition of a slave stimulation based on the presence and timing of intrinsic beats.

FIG. 10 shows a block diagram of an exemplary method 1000. In an implementation block 1004, a bi-ventricular pacing scheme is implemented. A decision block 1008 follows wherein a decision is made as to whether an intrinsic event has occurred in an alert period of a ventricular channel (e.g., a slave channel). If the decision block 1008 decides that no activity or event has occurred in an alert period, then the method 1000 proceeds to a continuation block 1010 where the bi-ventricular pacing scheme continues where, as appropriate, the method 1000 flows back to the decision block (e.g., after certain programmed events, etc.). However, if the decision block 1008 decides that an intrinsic event occurred in an alert period, then another decision block 1012 follows. The decision block 1012 decides if the activity or event occurred prior to a VV delay period (e.g., a $\Delta_{programmed}$). If the decision block 1012 decides that the occurrence was not prior to a VV delay period then the method 1000 continues in an inhibition block 1014 that inhibits delivery of a pace event to a ventricle (e.g., to a slave ventricle, see Case II as discussed above). However, if the decision block 1012 decides that the occurrence was prior to a VV delay period then the method 1000 continues in a trigger, blank and inhibition block 1016. The trigger, blank and inhibition block 1016 acts to trigger delivery of a pace to a ventricle (e.g., a master ventricle), to initiate one or more blanking periods (e.g., atrial and/or ventricular), and to inhibit delivery of a pace to another ventricle (e.g., a slave ventricle).

Of course, an alert period for a master ventricular channel may exist wherein an intrinsic event in the master ventricle causes inhibition of a scheduled pace event in the master ventricle and causes an update in the timing of a scheduled slave pace event. For example, if an intrinsic event is sensed or detected in the master ventricle, then the VV delay may commence in response thereto. Such an exemplary method would act to preserve the VV delay (e.g., $\Delta_{programmed}$) to ensure appropriate timing of contractions in left and right ventricles.

Various exemplary methods, devices and/or systems include setting an interchamber delay between a master chamber and a slave chamber. For example, an interventricular delay may determine timing of ventricular events while an interatrial delay may determine timing of atrial events. Accordingly, an exemplary method includes setting an interchamber delay between a master chamber and a slave chamber, sensing for cardiac activity, if the sensing senses intrinsic activity in the slave chamber, determining whether the intrinsic activity occurred during the interchamber delay, and if the intrinsic activity occurred before the interchamber delay, immediately delivering stimulation to the master chamber.

With respect to the ventricles, an exemplary method includes setting an interventricular (VV) delay between a master ventricle and a slave ventricle (e.g., setting $\Delta_{programmed}$) and sensing for ventricular activity. If activity is sensed in the slave ventricle prior to the VV delay period and hence prior to delivery of a pace to the master ventricle, then immediately delivering stimulation to the master ventricle and inhibiting delivery of stimulation to the slave ventricle. If activity is sensed in the slave ventricle after delivery of stimulation to the master ventricle and prior to expiration of the VV delay, then the exemplary method may inhibit delivery of stimulation to the slave ventricle. Such a method optionally includes adjusting the ventricular refractory period in the slave ventricle channel to be greater than the appropriate IVCD minus VV. IVCD could be either IVCD-LR or IVCD-RL or average of the two.

An exemplary implantable device includes a power supply, a processor, a lead including one or more electrodes capable of being positioned proximate to a master ventricle, a lead including one or more electrodes capable of being positioned proximate to a slave ventricle, and control logic, executable through use of the processor, to set an interventricular delay between the master ventricle and the slave ventricle and to call for immediate delivery of stimulation to the master ventricle using the lead proximate to the master ventricle upon detection of intrinsic activity in the slave ventricle prior to the interventricular delay (e.g., prior to delivery of stimulation to the master ventricle). Such control logic optionally inhibits delivery of stimulation to the slave ventricle.

Various exemplary methods, devices, systems, etc., may consider instances where normal atrio-ventricular conduction exists for one ventricle. For example, if an atrio-ventricular conduction time for the right ventricle does not exceed one or more limits representative of normal conduction, then the atrio-ventricular time for the right ventricle may serve as a basis for determining an appropriate time for delivery of stimulation to the left ventricle (or vice versa). The following equation (Eqn. 14) may be used in such a situation:

$$AV_{LV}=AR_{RV}-|\Delta| \text{ or } PV_{LV}=PR_{RV}-|\Delta| \tag{14}$$

Eqn. 14 is similar to the equation used in blocks 928' and 940' of Scenario IB of FIG. 9. With respect to backup pulses, a backup pulse (e.g., for purposes of safety, etc.) may be set according to the following equation (Eqn. 15):

$$AV_{RV}=AR_{RV}+|\gamma| \text{ or } PV_{RV}=PR_{RV}+|\gamma| \tag{15}$$

Of course, administration of a backup pulse may occur upon one or more conditions, for example, failure to detect activity in the particular ventricle within a given period of time. In Eqn. 15, the parameter γ is a short time delay, for example, of approximately 5 ms to approximately 10 ms. Eqn. 15 is similar to the equation used in blocks 918' and 930' of Scenario IB of FIG. 9.

According to Eqn. 14, there may not be an a priori need for a particular $AV_{optimal}$ or $PV_{optimal}$. Instead, a need may exist for one or more limits to determine if a sensed AR or PR may be considered normal or acceptable. Further, in such exemplary methods, devices, systems, etc., an alert period may be implemented where sensing or detection of an intrinsic event in a channel associated with the scheduled pace event causes inhibition of the pace event. For example, if an alert period exist prior to the scheduled pace event and intrinsic activity is detected then inhibition of the pace event may occur, which may act to conserve energy of an implanted device. However, if the alert period expires without sensing or detecting intrinsic activity, the back up pacing pulse in the right ventricle is delivered at $AV_{RV}$ and $AV_{LV}$ (e.g., as scheduled).

In many instances, heart condition will affect $AR_{RV}$ and $AR_{LV}$, and IVCD, which, in turn, may affect an existing optimal VV delay setting. Various exemplary methods, devices, systems, etc., include triggering of an algorithm to update an existing optimal VV delay according to a predetermined time or event period or activity sensors for exercise, resting, etc. An exemplary device may include a learning method that learns based on differences in conduction times (e.g., $AR_{RV}$ and $AR_{LV}$, IVCD, etc.) such that parameters associated with different heart demands can be stored. The exemplary learning method may then extract such learned or other parameters to set an optimal VV delay.

In the aforementioned learning example, if the device learns on the basis of different cardiac demands, the device may adjust AV delay and/or VV delay and/or learn a new AV delay and/or VV delay upon a change in cardiac demand. According to this example, use of external measurement or sensing equipment (e.g., echocardiogram, etc.) is optional. Further, use of internal measurement or sensing equipment for sensing pressure or other indicators of hemodynamic performance is optional. Again, adjustment and learning may rely on IEGM information and/or cardiac other rhythm information.

An exemplary method relies on an atrial to right ventricular conduction time, an atrial to left ventricular conduction time and a α parameter, for example, as described above, to determine an optimal AV delay and/or VV delay. Another exemplary method relies on an atrial to right ventricular conduction time, an atrial to left ventricular conduction time and a limit that may be used to decide whether one or more of the conduction times are acceptable. In these examples, an interventricular conduction time may be used in lieu of an atrial to ventricular conduction time, for example, where ventricular activity originates with a common atrial event.

According to various exemplary methods, devices, systems, etc., information acquired (e.g., sensed, detected and/or determined) may be used to diagnose cardiac condition. For example, an exemplary method may track AV delays and/or VV delays over time. Such information may then be used to determine subsequent therapy.

Various exemplary methods, devices, systems, etc., include determining an optimal interventricular delay (e.g., $\Delta_{optimal}$) using a modality such as an echocardiogram. While an internal echocardiogram or implantable hemodynamic sensors may be available or become available and be able to measure such optimal delays for a variety of patient circumstances (e.g., sleep, exercise, etc.), an exemplary method, device, system, etc., includes use of one or more internal sensors to measure and/or update such an optimal delay and/or to determine values for one or more parameters related to an optimal delay. For example, a blood pressure sensor (e.g., aortic arch, etc.) may be used to determine or to update an optimal delay. Further, information may be collected over a period of time to determine heart condition (e.g., deterioration, improvement, etc.).

In general, an optimal interventricular delay will change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

As described herein, various techniques include adjusting one or more pacing parameters based at least in part on patient activity. Such techniques may use variables discussed with respect to FIG. 4 and shown in FIG. 6, in particular, the variables ΔP, ΔA, DD and/or AD may be used. Two parameters, δ and β, are discussed in more detail below. The parameter δ may depend on ΔP or ΔA while the parameter β may depend on δ and DD or AD, as indicated by the following equations (Eqns. 16 and 17):

$$\delta = f(\Delta P) \text{ or } f(\Delta A) \quad (16)$$

$$\beta = \delta/DD \text{ or } \delta/AD \quad (17)$$

These parameters may be used to determine one or more pacing parameters, for example, as indicated by the following equations (Eqns. 18 and 19):

$$PV = \Delta P + \beta * DD \quad (18)$$

$$AV = \Delta A + \beta * AD \quad (19)$$

Variations of the Eqns. 16-19 are discussed in more detail with respect to FIGS. 11-20. The PV or AV of Eqns. 18 and 19 may be used to determine an optimal PV or AV. For example, $AV_{opt}$ may be determined using Eqn. 19 and then used in any of the various scenarios of FIG. 9. For VV delay, techniques described above may be used. However, as discussed in more detail below, VV may depend on activity and hence may change when activity state changes. VV is used for bi-ventricular pacing and the following equations (Eqns. 20 and 21) may be used:

$$PV'' = PV' + VV \quad (20)$$

$$AV'' = AV' + VV \quad (21)$$

where PV' and AV' are for the master ventricle and where PV" and AV" are for the slave ventricle.

Figure 11:
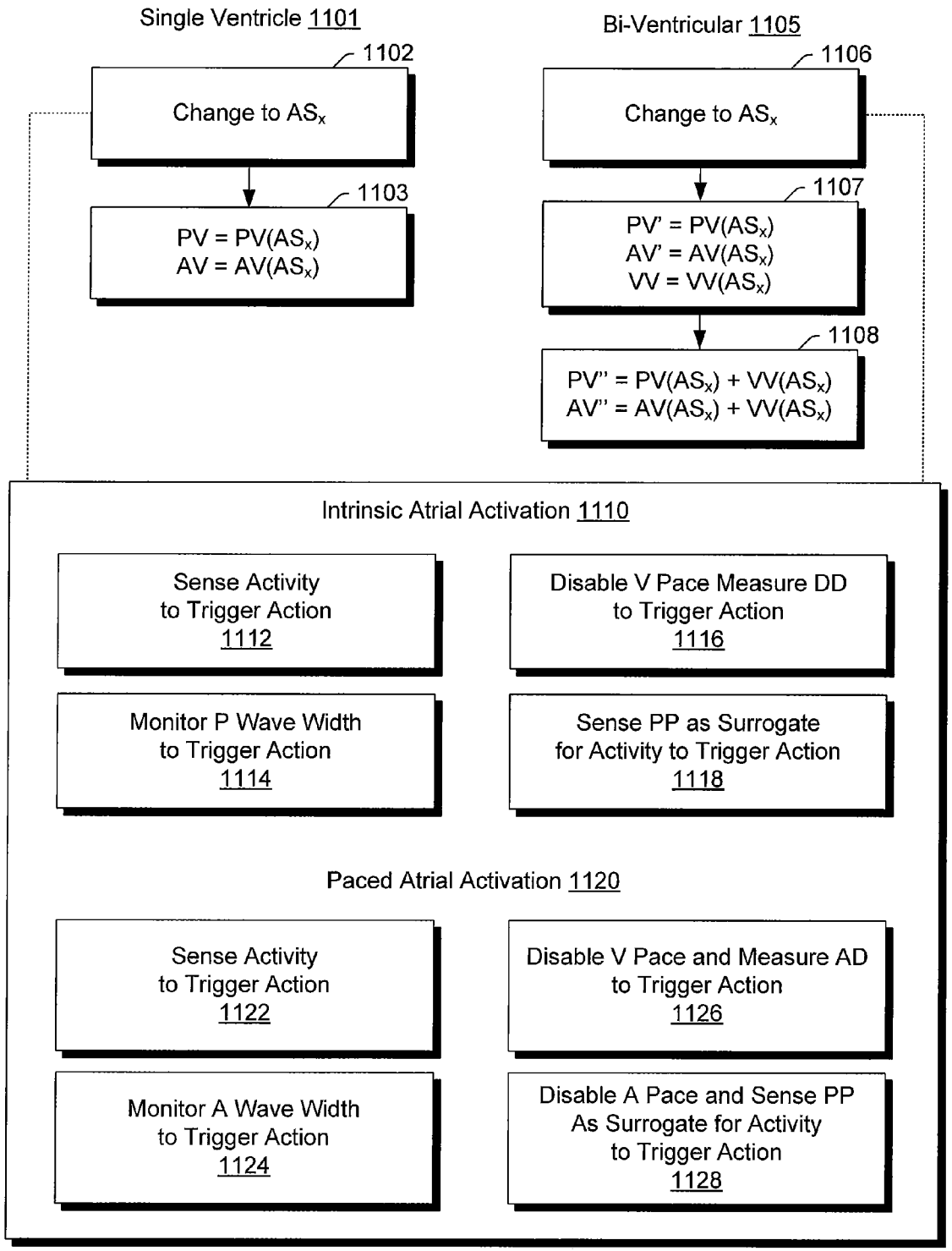
FIG. 11 is a block diagram of various exemplary schemes that can be used to improve pacing in relationship to patient activity state.

FIG. 11 shows exemplary methods 1100 for optimizing pacing therapy. A general method 1101 pertains to pacing of a single ventricle while another general method 1105 pertains to bi-ventricular pacing. The method 1101 commences in a change block 1102 where a change in activity state is noted, for example, a change from an activity state $AS_1$ to an activity state $AS_2$. For purposes of generality, the subscript "x" is used to represent a particular activity state ($AS_x$) from a set of two or more activity states (e.g., $AS_0, AS_1, \ldots AS_N$). In response to a change in activity state, the method 1101 enters an update block 1103 that updates PV or AV based at least in part on the present activity state (i.e., $AS_x$).

The method 1105 operates in a similar manner to the method 1101, except that updates occur for both ventricles. The method 1105 commences in a change block 1106 where a change in activity state is noted. In response to a change in activity state, the method 1105 enters an update block 1107 that updates PV or AV for the master ventricle (PV' or AV') and that updates the interventricular delay VV, if desired. Another update block 1108 updates PV or AV for the slave ventricle using the updated PV or AV for the master ventricle and a VV value, which may depend on activity state.

As both method depend on a change in activity state, various schemes are presented where one set of schemes 1110 pertains to intrinsic atrial activation while another set of schemes 1120 pertains to paced atrial activation. As described herein, various exemplary methods may include sensing patient activity, directly or indirectly, and adjusting one or more pacing parameters based at least in part on such sensing.

The schemes 1112, 1122 include sensing patient activity, for example, using an activity sensor (e.g., accelerometer, minute ventilation, etc.), and adjusting one or more pacing parameters based at least in part on such sensing. The schemes 1112, 1122 may be used regardless of whether a therapy relies on atrial pacing. An exemplary method may select a pacing parameter for a pacing therapy based on patient activity state. For example, an implantable device may include a set of parameters for a rest state and a set of parameters for an exercise state.

The schemes 1114, 1124 include monitoring one or more characteristics of atrial activity and adjusting one or more pacing parameters based at least in part on such monitoring. For example, the scheme 1114 includes monitoring P wave width (e.g., $\Delta P$) and using P wave width to adjust one or more pacing parameters whereas the scheme 1124 includes monitoring A wave width (e.g., $\Delta A$) and using A wave width to adjust one or more pacing parameters. As explained with respect to FIG. 4, P wave width or A wave width may increase as patient activity increases. Thus, if the P wave width or the A wave width exceed a limit, then an exemplary method may call for a change in one or more pacing parameters.

The schemes 1116, 1126 include disabling ventricular pacing and measuring DD interval or AD interval, respectively, and adjusting one or more pacing parameters based at least in part on such measuring. As explained with respect to FIG. 4, DD interval or AD interval may increase as patient activity increases. Thus, if the DD interval (e.g., $DD_{RV}$ or $DD_{LV}$) or the AD interval (e.g., $AD_{RV}$ or $AD_{LV}$) exceed a limit, then an exemplary method may call for a change in one or more pacing parameters.

The scheme 1118 includes sensing PP interval as a surrogate for patient activity and adjusting one or more pacing parameters based at least in part on such sensing. In general, PP interval will decrease as patient activity increases; noting that certain conditions or drugs may make this technique less useful (e.g., beta blockers, high NYHA class, etc.). While PP interval is mentioned, other intervals may be used based on a marker that occurs once per cardiac cycle (e.g., $R_{RV}$, $R_{LV}$, etc.). An exemplary method may select a pacing parameter for a pacing therapy based on an interval. For example, an implantable device may include a set of parameters for a long interval (e.g., a rest state) and a set of parameters for a short interval (e.g., an exercise state).

While the foregoing discussion of the various schemes 1100 pertains to schemes individually, an exemplary method may use any of the various schemes 1100, as appropriate. For example, an exemplary method may include monitoring P wave width and disabling ventricular pacing to measure DD interval based at least in part on P wave width.

FIG. 12 shows various exemplary methods 1200. While equations are presented, implementation of techniques described herein may be implemented using any of a variety of forms of control logic. For example, look-up tables may be used together with logic that stores and/or pulls data from the look-up table. Control logic to achieve the overall goals achieved by the various equations 1200 may be achieved by control logic that does not explicitly rely on the equations, as presented.

A state block 1210 defines various activity states. The activity states include a base state, for example, a rest state denoted by a subscript "0". In other examples, the subscript "rest" is used. The activity states include at least two states, for example, a base state and another activity state. In FIG. 12, the states range from the base state to activity state "N", which may be an integer without any numeric limitation (e.g., N may equal 5, 10, 100, 1000, etc.). The number of activity states may depend on patient condition and patient activity. For example, a patient that is bedridden may have few activity states when compared to a young patient (e.g., 40 years old) fitted with a pacemaker that leads an active life with a regular exercise regimen.

A PV or AV states block 1220 presents equations for the parameters $\beta$ and $\delta$ as well as for a base state PV and AV and PV and AV for a state other than a base activity state, referred to as $AS_x$, where x=1, 2, ... N. In addition, sets of equations are presented that include a pacing latency term PL. Pacing latency is generally defined as the time between delivery of a cardiac stimulus and time of an evoked response caused by the stimulus. More specifically, an implantable device may use the time of delivery of a stimulus and the time at which a sensed, evoked response signal deviates from a baseline, which is referred to herein as $PL_I$ (e.g., to initiation of evoked response). Such a signal is usually sensed using the lead that delivered the stimulus, however, electrode configuration may differ (e.g., unipolar delivery and bipolar sensing, bipolar delivery and unipolar sensing, etc.). In some instances, the pacing latency may exceed 100 ms due to ischemia, scarring, infarct, etc. Thus, PV or AV timing may be adjusted accordingly to call for earlier delivery of a stimulus to a ventricle or ventricles.

An exemplary algorithm may determine PL for the right ventricle (for a right ventricular lead) and for the left ventricle (for a left ventricular lead) during measurement of IVCD-LR and IVCD-RL (e.g., parameters that may be used to determine VV). While pacing latency can be measured from the time of delivering a pacing pulse to the time of an evoked response at the pacing lead ($PL_I$), pacing latency may be measured alternatively from the time of the pulse to the peak of an evoked response ($PL_{Peak}$). In either instance, such techniques may shorten block and/or discharge periods, optionally to a minimum (e.g., about 3 ms in some commercial ICDs). An algorithm may also provide for detection of capture, for example, using an integral (e.g., PDI) and/or a derivative (e.g., $D_{max}$). In general, pacing latencies for LV and RV leads correspond to situations where capture occurs. In yet another alternative, during P wave and PR measurement, a time delay from a marker of a sensed R event to the peak of a QRS complex may be measured and used as a correction term akin to pacing latency.

A VV states block 1230 presents equations for the parameters $\alpha$, $\Delta$ and $\Delta_{IVCD}$ and VV for a base activity state ($AS_0$) and another activity state ($AS_x$). Theses equations may be used in various scenarios of the method 900 of FIG. 9. Noting that some differences exist, for example, lack of absolute values the parameter $\Delta$. To account for this variation, the value of $\Delta$ is used to determine whether the right ventricle or left ventricle is paced for single ventricle pacing or is the master for bi-ventricular pacing. If the $\Delta$ is less than 0 ms, then the right ventricle is paced or the master whereas if $\Delta$ is greater than 0 ms, then the left ventricle is paced or the master. For bi-ventricular pacing, the PV or AV state equation is used for the master ventricle and then the VV equation is used to determine timing of the slave ventricle. Hence, the control logic uses $\Delta$ to determine whether the PV or AV state equation will correspond to the left ventricle or the right ventricle.

The block 1230 also includes equations for a pacing latency differential, referred to as $\Delta PL$. This term may be calculated, for example, as the difference between $PL_{Peak}$ and a generic or average pacing latency (e.g., $PL_{Ave}$ based on a sampling of "normal" pacing latencies). Hence, $\Delta PL$ may represent a difference from a normal pacing latency. A normal pacing latency may be around 70 ms and hence ΔPL may equal $PL_{Peak}$ minus 70 ms. The parameter APL may be calculated for both the right ventricle (e.g., ΔPL-RV) and the left ventricle (e.g., ΔPL-LV). Where VV has positive sign that indicates to pace LV first, then the correction term ΔPL-LV may be added while where VV has a negative sign that indicates to pace RV first then the correction term ΔPL-RV may be added. In block 1230, the term ΔPL is shown without indication of LV or RV, noting that use of ΔPL-LV or ΔPL-RV may be determined accordingly. A criterion or criteria may be used to decide if a pacing latency correction term should be used in determining PV, AV or VV. For example, if PL exceeds a certain limit, then a pacing latency correction term or terms may be used. Similarly, if ΔPL exceeds a certain limit, then a pacing latency correction term or terms may be used.

Figure 13:
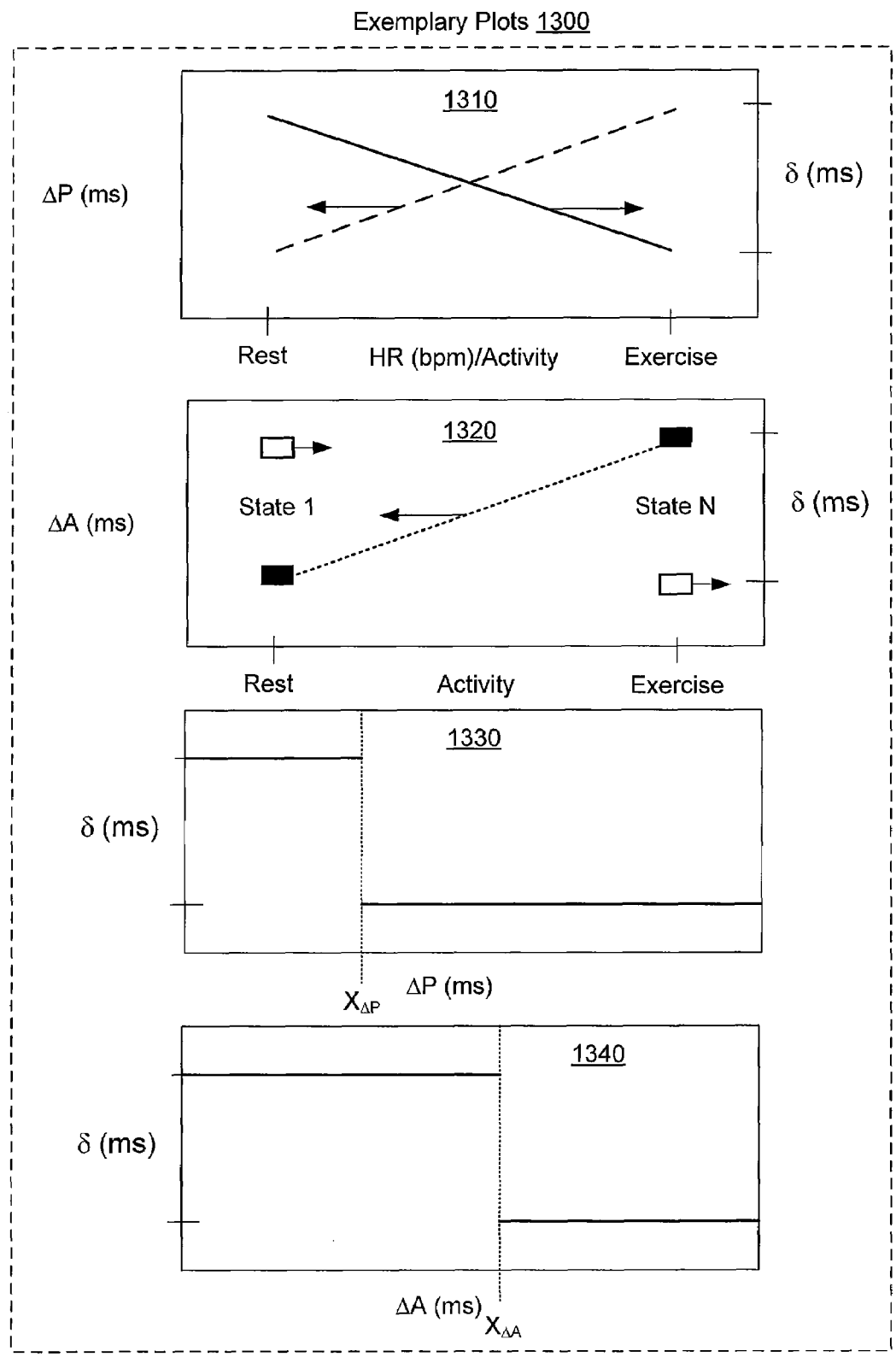
FIG. 13 is a series of plots for a parameter $\delta$, for use in determining one or more pacing parameters.

FIG. 13 shows a series of plots 1300 that pertain to a parameter δ that can be used to adjust one or more pacing parameters. Referring to FIG. 12, the parameter δ appears in the PV or AV state equations 1220. A plot 1310 of P wave width (ΔP) and the parameter δ versus heart rate or patient activity. The plot 1310 indicates that, as activity increases, ΔP increases and δ decreases. Such a relationship may be used by an implantable device to adjust the parameter δ based on heart rate or patient activity or ΔP.

A plot 1320 of A wave width (ΔA) and the parameter δ versus patient activity. The plot 1320 indicates that, as activity increases, ΔA increases and δ decreases. The plot 1320 shows a state based approach where a series of activity states (e.g., State 1 to State N) correspond to particular values for the parameter δ. Such a state based approach may be used by an implantable device to adjust the parameter δ based on heart rate or patient activity or ΔA.

A plot 1330 of parameter δ versus ΔP indicates a change in δ based on a ΔP limit, $X_{ΔP}$. Where ΔP falls below the limit $X_{ΔP}$, δ assumes a high value; whereas, when ΔP equals or exceeds the limit $X_{ΔP}$ δ assumes a low value. Similarly, a plot 1340 of parameter δ versus ΔA indicates a change in δ based on a ΔA limit, $X_{ΔA}$. Where ΔA falls below the limit $X_{ΔA}$, δ assumes a high value; whereas, when ΔA equals or exceeds the limit $X_{ΔA}$ δ assumes a low value.

Figure 14:
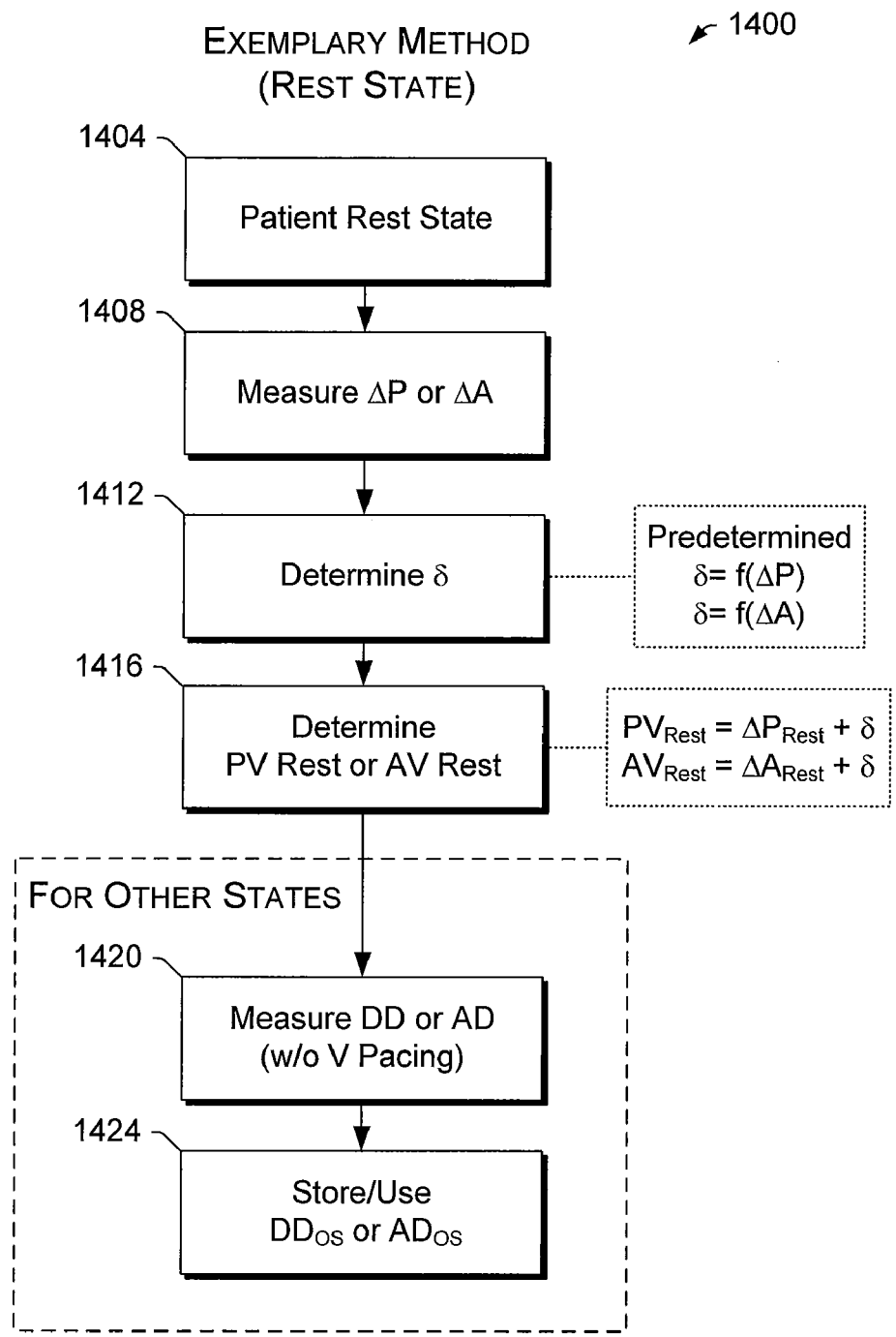
FIG. 14 is a block diagram of an exemplary method for initializing parameters for a rest state and optionally another activity state.

FIG. 14 shows an exemplary method 1400 for initialization of rest state parameters. The method 1400 commences in an activity block 1404 that confirms a patient is in a rest state. Once the patient is in a rest state, a measurement block 1408 measures the width of a P wave or in an A wave, as appropriate. A determination block 1412 follows that determines a value for the parameter δ based at least in part on the measured P wave or A wave width. The relationship between P wave width or A wave width and the parameter δ may be predetermined (see, e.g., the plots 1300 of FIG. 13). After determination of a value for the parameter δ, the method 1400 enters another determination block 1416 that determines a value for a rest state PV ($PV_{Rest}$) or a rest state AV ($AV_{Rest}$), as appropriate. In this example, $PV_{Rest}=ΔP_{Rest}+δ$ while $AV_{Rest}=ΔA_{Rest}+δ$, as the term $β*DD_{Rest}$ or $β*AD_{Rest}$ simplifies to δ (see, e.g., Eqns. 16-19). As already mentioned with respect to block 1220 of FIG. 12, a pacing latency correction term may be used to determine PV or AV.

The exemplary method 1400 may then take action for other activity states. For example, a measurement block 1420 measures the interval DD or AD, without ventricular pacing (e.g., disabling ventricular pacing for one or both ventricles), and a storage or use block 1424 stores or uses the measured, other state DD interval ($DD_{OS}$) or AD interval ($AD_{OS}$) for determining one or more pacing parameters. The method 1400 may also provide for determining rest state values of parameters associated with VV, for example, where bi-ventricular pacing is used or may be used. Alternatively, even if bi-ventricular pacing is not used, such information may be collected for purposes of assessing cardiac condition and optionally for assessing parameters for other patients that may benefit from bi-ventricular pacing therapies or that are already being treated with bi-ventricular pacing therapy.

Figure 15:
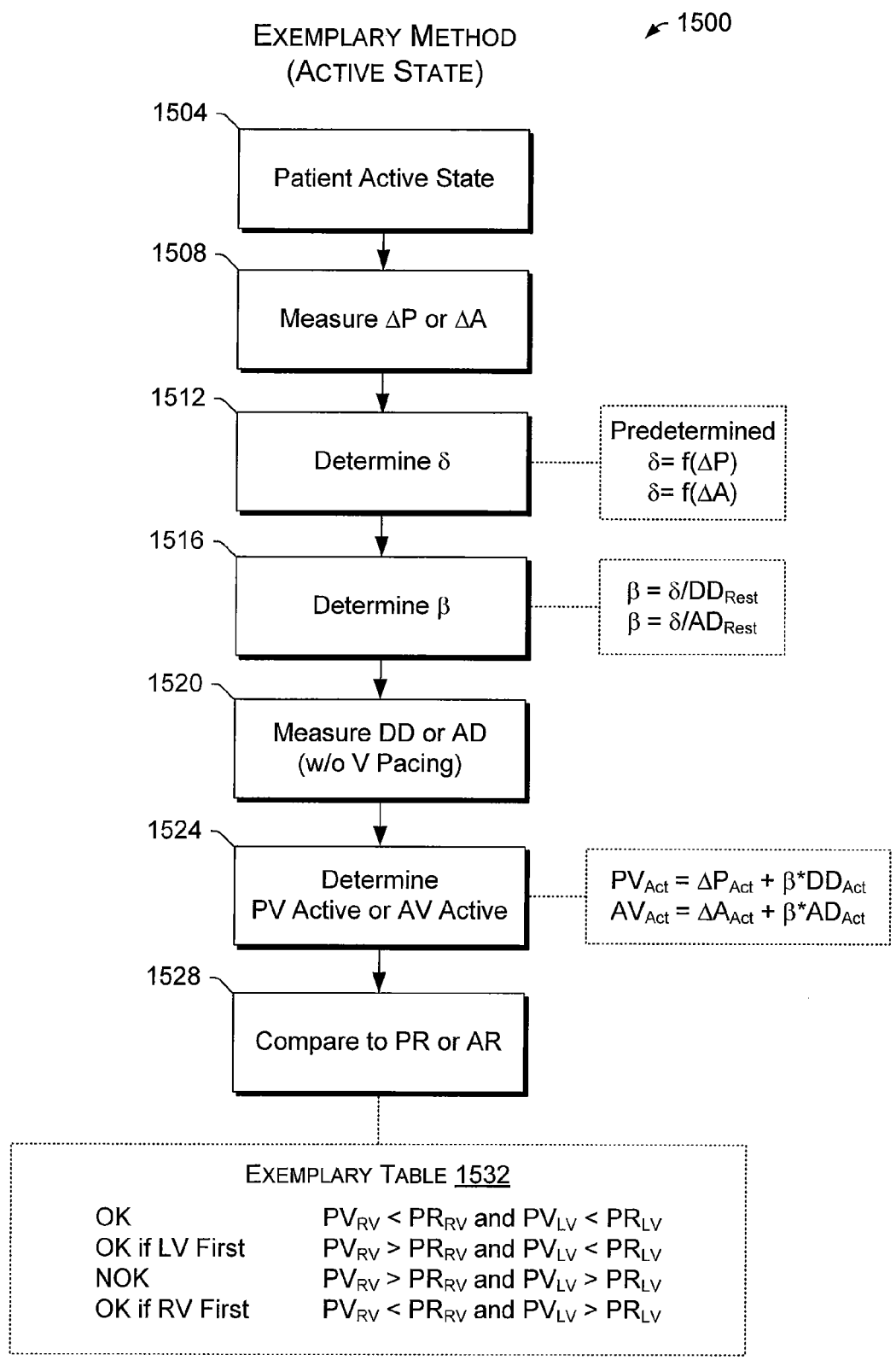
FIG. 15 is a block diagram of an exemplary method for initializing parameters for an active state (e.g., an exercise state).

FIG. 15 shows an exemplary method 1500 for initialization of active state parameters. The method 1500 commences in an activity block 1504 that confirms a patient is in an active state such as an exercise state. For example, a care provider, a device, etc., may instruct a patient to exercise and, once the patient achieves a certain activity level, then the method 1500 may commence. Once the patient achieves the desired level of activity, a measurement block 1508 measures the width of a P wave or in an A wave, as appropriate. A determination block 1512 follows that determines a value for the parameter δ based at least in part on the measured P wave or A wave width. The relationship between P wave width or A wave width and the parameter δ may be predetermined (see, e.g., the plots 1300 of FIG. 13). After determination of a value for the parameter δ, the method 1500 enters another determination block 1516 that determines a value for the parameter β, which depends on the value for the parameter δ (see, e.g., Eqns. 16-17). Next, a measurement block 1520 measures the interval DD or AD, without ventricular pacing (e.g., disabling ventricular pacing for one or both ventricles), and a storage or use block 1524 stores or uses the measured, active state DD interval ($DD_{Act}$) or AD interval ($AD_{Act}$) for determining one or more pacing parameters. In the example of FIG. 15, the determination block 1524 determines $PV_{Act}$ or $AV_{Act}$ according to Eqn. 18 or Eqn. 19 (e.g., $PV_{Act}=ΔP_{Act}+β*DD_{Act}$ or $AV_{Act}=ΔA_{Act}+β*AD_{Act}$). In addition, as already mentioned with respect to block 1220 of FIG. 12, a pacing latency correction term may be used to determine PV or AV. As explained below, $PV_{Act}$ or $AV_{Act}$ may be used once a patient achieves a certain level of activity. Other techniques may measure ΔP or ΔA or DD or AD and then determine PV or AV, as appropriate.

Once the determination block 1524 determines $PV_{Act}$ or $AV_{Act}$ for one or both ventricles, then an assessment block 1528 assess the value or values with respect to PR or AR for one or both ventricles. Such an assessment may occur using a measured PR or AR values or by implementing the determined PV or AV values and deciding whether an event occurred prior to a ventricular paced event for one or both ventricles. Referring again to FIG. 15, a table 1532 indicates when a PV or an AV value may be used. In general, the PV or AV value for a ventricle should be less than the intrinsic PR or AR value to ensure that pacing controls; noting that for some therapies, intrinsic activity may be preferred under certain circumstances. As indicated by the table 1532, whether a value is "OK" may depend on which ventricle is paced when only one ventricle is paced or which ventricle is paced first when both ventricles are paced. Such an assessment may occur as appropriate using the table 1532 or other suitable table or assessment.

The method 1500 may also provide for determining active state values of parameters associated with VV, for example, where bi-ventricular pacing is used or may be used. Alternatively, even if bi-ventricular pacing is not used, such information may be collected for purposes of assessing cardiac condition and optionally for assessing parameters for other patients that may benefit from bi-ventricular pacing therapies or that are already being treated with bi-ventricular pacing therapy.

Figure 16:
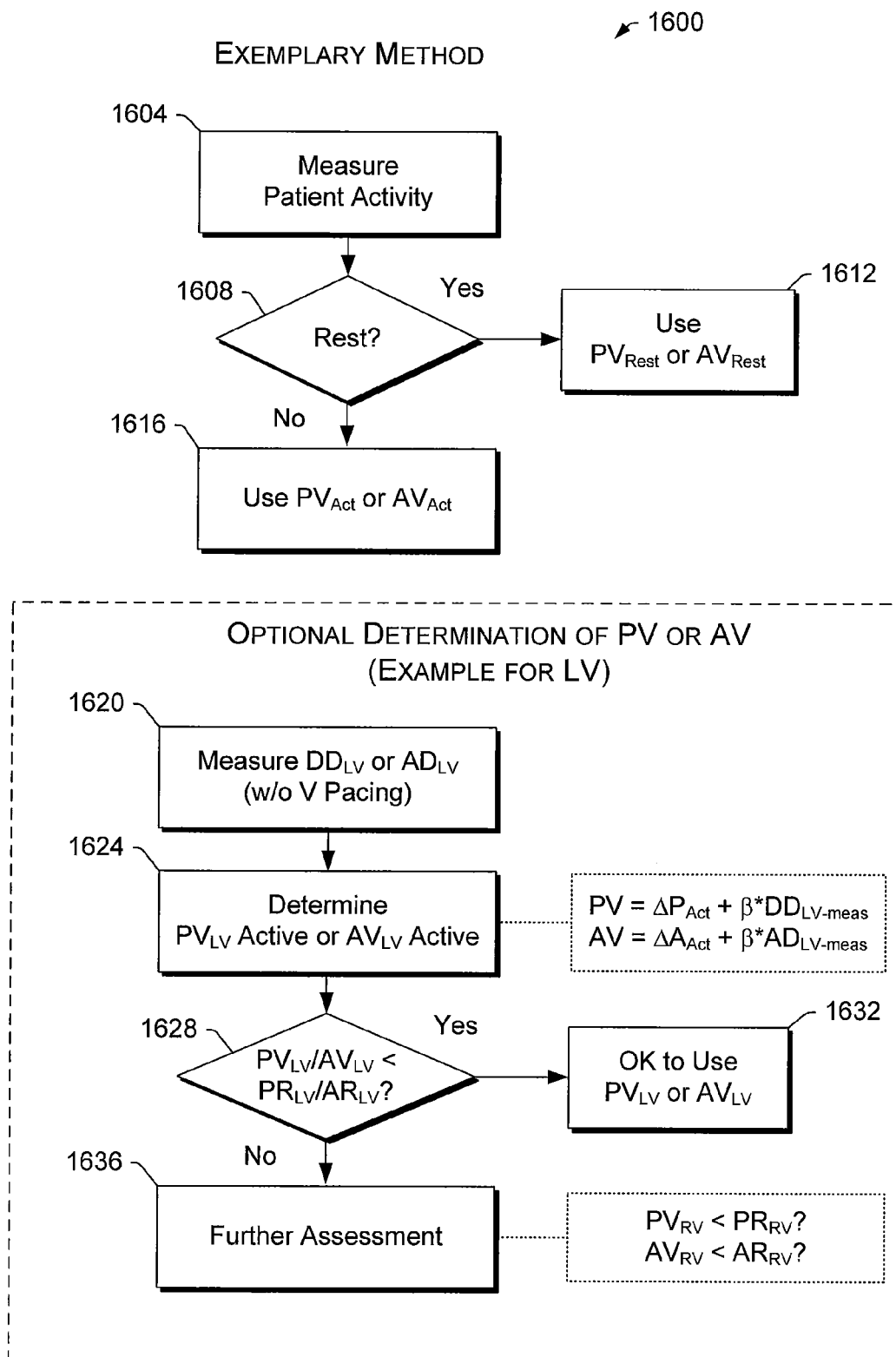
FIG. 16 is a block diagram of an exemplary method that may rely on the methods of FIGS. 14 and 15.

FIG. 16 shows an exemplary method 1600 that may rely on the method 1400 and/or the method 1500 for appropriate PV or AV values. The method 1600 may require validation of rest state values and/or active state values prior to implementation. As shown in FIG. 16, the method 1600 commences in a measurement block 1604 that measures a patient's activity. A decision block 1608 follows that decides if, based on the measured activity, the patient is in a rest state. For example, the measurement block 1604 may rely on a motion sensor and the decision block 1608 may use a motion limit that distinguishes a patient rest state from one or more other patient activity states. If the decision block 1608 decides that the patient is at rest, then the method 1600 uses a predetermined $PV_{Rest}$ or $AV_{Rest}$ value, per the use block 1612. Otherwise, the method 1600 uses a predetermined $PV_{Act}$ or $AV_{Act}$ value, per the use block 1616, where the subscript "Act" represents a patient activity state other than a rest state.

FIG. 16 also shows several additional, optional action blocks 1620, 1624, 1628 which may be used, for example, following the decision block 1608 if the measured activity is not indicative of a rest state. In this example, LV pacing is assumed and the determined values for $PV_{Act}$ or $AV_{Act}$ are for the left ventricle.

A measurement block 1620 measures the $DD_{LV}$ interval ($DD_{meas-LV}$) or $AD_{LV}$ interval ($AD_{meas-LV}$), while pacing to the left ventricle or both ventricles is disabled. A determination block 1624 uses the measured DD interval or AD interval to determine $PV_{LV}$ or $AV_{LV}$, for example, according to Eqn. 18 or Eqn. 19 (e.g., $PV_{LV}=\Delta P_{Act}+\beta *DD_{meas-LV}$ or $AV_{LV}=\Delta A_{Act}+\beta *AD_{meas-LV}$). In using Eqn. 18 or Eqn. 19, the value for $\Delta P$ or $\Delta A$ may be predetermined or a method may measure $\Delta P$ or $\Delta A$, as explained below with respect to FIG. 17. As already mentioned with respect to block 1220 of FIG. 12, a pacing latency correction term may be used to determine PV or AV.

After the determination block 1624, a decision block 1628 decides if the $PV_{LV}$ or $AV_{LV}$ value is less than $PR_{LV}$ or $AR_{LV}$, respectively. If the value is less than the conducted value, then an OK block 1632 indicates that use of the value is OK for LV pacing. In this instance, pacing will control assuming that the PR or AR value does not become less than the PV or AV value. If the decision block 1628 decides that $PV_{LV}$ or $AV_{LV}$ is not less than $PR_{LV}$ or $AR_{LV}$, respectively, then further assessment occurs in an assessment block 1636. Such further assessment may determine and/or measure right ventricular values. The table 1532 of FIG. 15 may be used for purposes of assessing one or more pacing parameter values.

The method 1600 may also provide for determining whether to use rest state or active state VV, for example, where bi-ventricular pacing is used or may be used (e.g., per blocks 1612 and 1616). Alternatively, even if bi-ventricular pacing is not used, such information may be collected for purposes of assessing cardiac condition and optionally for assessing parameters for other patients that may benefit from bi-ventricular pacing therapies or that are already being treated with bi-ventricular pacing therapy.

Figure 17:
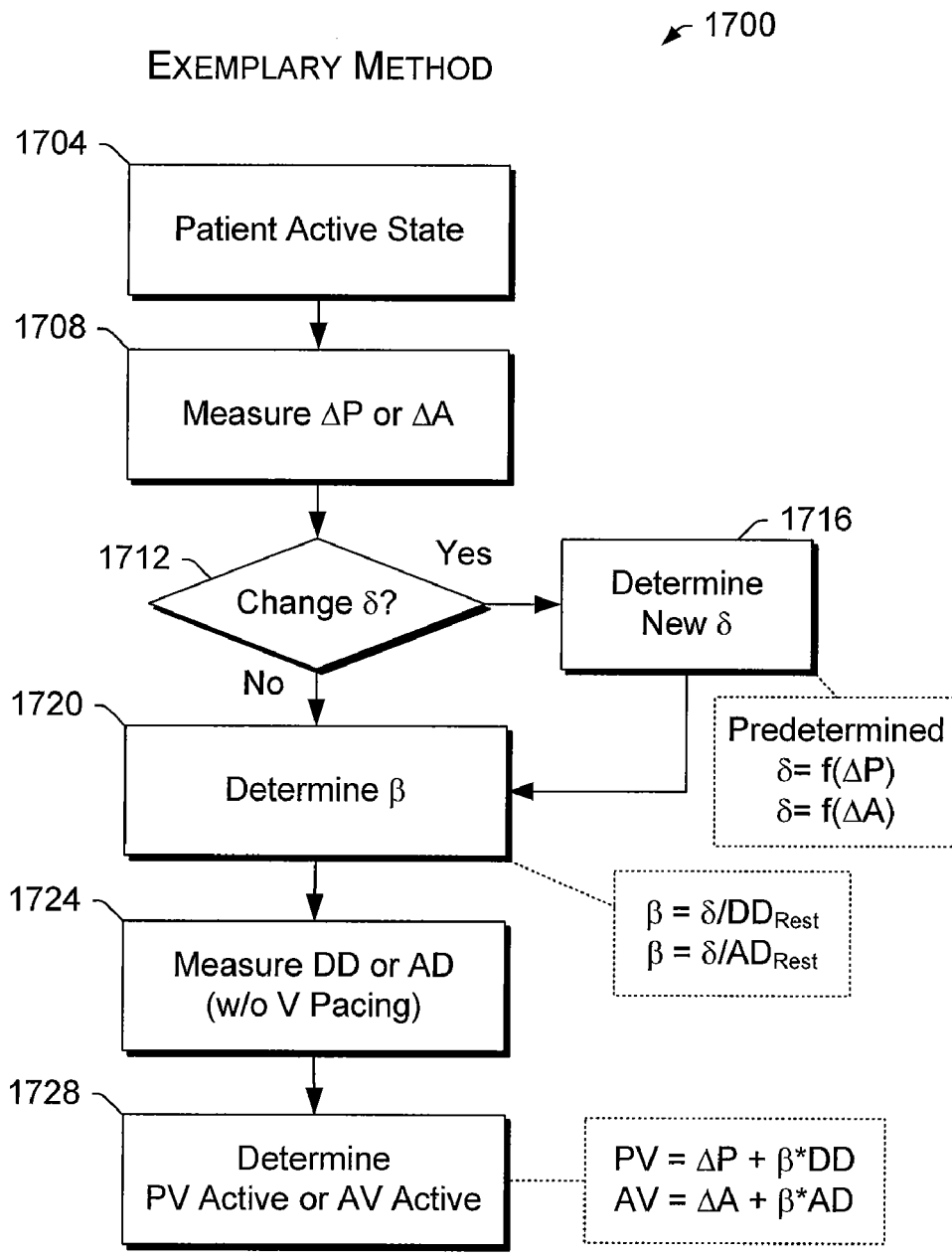
FIG. 17 is a block diagram of an exemplary method that decides if a change should occur for the parameter $\delta$, for example, based on a P wave width or an A wave width.

FIG. 17 shows an exemplary method 1700 for determining one or more pacing parameters. The method 1700 commences in an activity block 1704 that confirms a patient is in an active state such as an exercise state. A measurement block 1708 follows that measures the width of a P wave or in an A wave, as appropriate. In other examples, measurement of P wave width or A wave width may be used to determine level or patient activity, for example, where a relationship exists between P wave width or A wave width and patient activity (see, e.g., the plots 1310, 1320 of FIG. 13).

After measurement of $\Delta P$ or $\Delta A$, a decision block 1712 decides whether a change in the value of the parameter $\delta$ should occur. For example, the plots 1330, 1340 indicate that the value of $\delta$ may be related to the value of $\Delta P$ or $\Delta A$, hence, the decision block 1712 may use a limit such as $X_{\Delta P}$ or $X_{\Delta A}$ to decide if a change should occur for the value of $\delta$. If the decision block 1712 decides that a change should occur, then the method 1700 enters a determination block 1716 that determines a new value for $\delta$. Otherwise the method 1700 proceeds to a determination block 1720 for the parameter $\beta$. In either instance, the method 1700 proceeds to the determination block 1720.

In the example of FIG. 17, after the method 1700 determines $\beta$, a measurement block 1724 measures the interval DD or AD, where ventricular pacing to one or both ventricles is disabled for purposes of such measurement (or measurements). A determination block 1728 follows that determines PV or AV according to Eqn. 18 or Eqn. 19 (e.g., $PV=\Delta P+\beta *DD_{meas}$ or $AV=\Delta A+\beta *AD_{meas}$) where $\Delta P$ or $\Delta A$ may rely on a value measured per block 1708 or on another value such as a rest state value ($\Delta P_{Rest}$ or $\Delta A_{Rest}$) or other activity state value ($\Delta P_{OS}$ or $\Delta A_{OS}$). As already mentioned with respect to block 1220 of FIG. 12, a pacing latency correction term may be used to determine PV or AV.

The method 1700 may also provide for determining activity state values for VV, for example, where bi-ventricular pacing is used or may be used. Alternatively, even if bi-ventricular pacing is not used, such information may be collected for purposes of assessing cardiac condition and optionally for assessing parameters for other patients that may benefit from bi-ventricular pacing therapies or that are already being treated with bi-ventricular pacing therapy.

Figure 18:
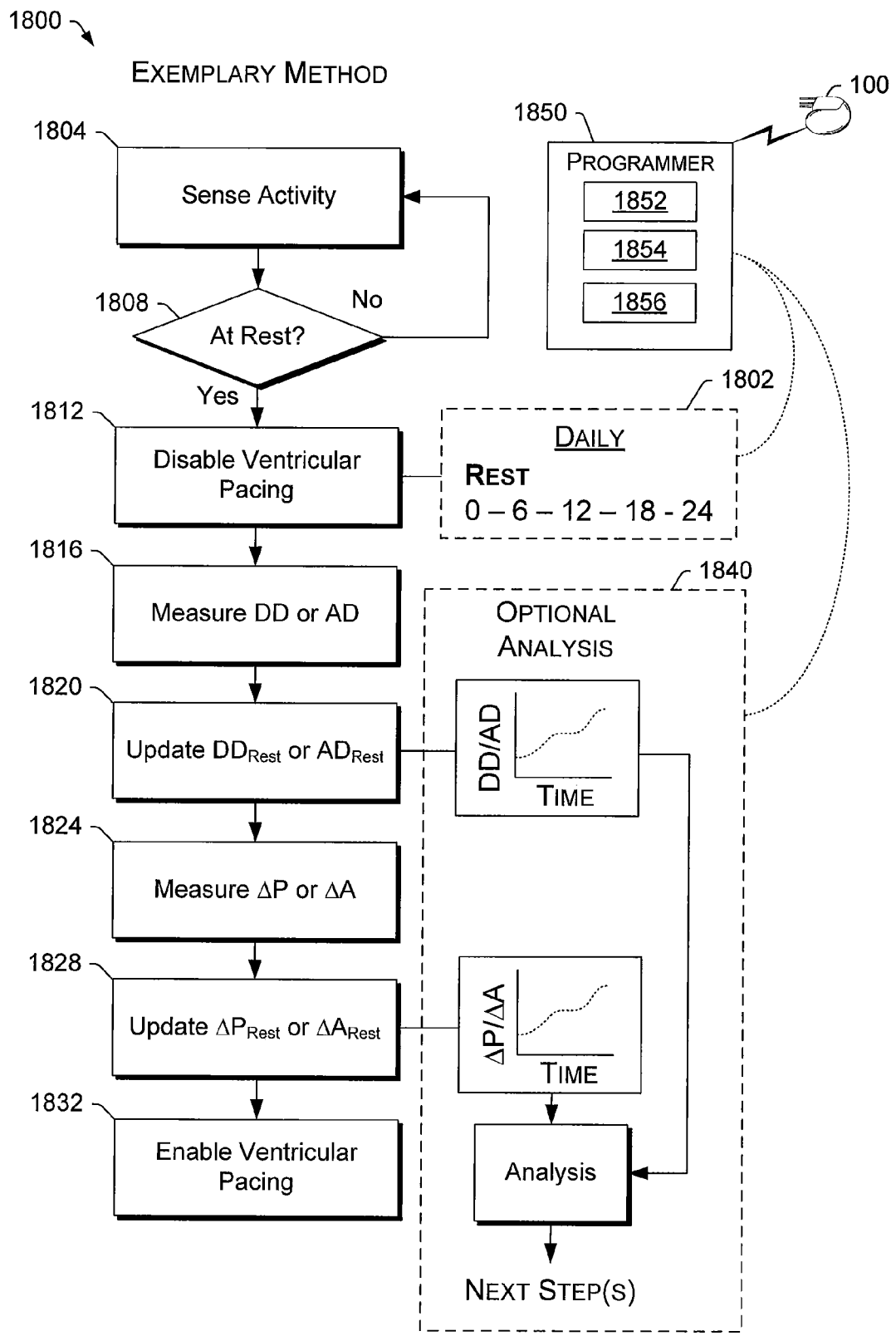
FIG. 18 is a block diagram of an exemplary method for updating one or more parameters based at least in part on a patient's activity state such as a rest state (e.g., sleep, etc.).

FIG. 18 shows an exemplary method 1800 that may be used to update one or more parameters for use in an equation to determine one or more pacing parameters. An optional analysis method 1840 may use updated information in any of a variety of analyses, for example, to assess cardiac condition, adjust therapy, etc. An optional computing device 1850 configured for programming an implantable device 100 may be used to perform the analysis method 1840, for example, using information acquired from the implantable device 100 where the implantable device 100 includes control logic for implementing the method 1800. The programmer 1850 includes telemetry circuitry 1852 for communicating with an implantable device, a processor 1854 and memory 1856, which may store processor-executable instructions to perform the analysis 1840 or other methods. The programmer 1850 may include features of a commercially available programmer (e.g., the Model 3510 programmer and model 3307 software or the MERLIN™ programmer and software marketed by St. Jude Medical, Sylmar, Calif.).

The method 1800 may commence according to a schedule 1802. For example, a clinician may use a programmer to program an implantable device (e.g., the device 100 of FIGS. 1 and 2) to update one or more parameters on a daily or other basis. The optional computing device 1850 may be used to schedule (per block 1802) an implantable device 100 where the implantable device includes control logic for implementing the method 1800. The programmer 1850 includes telemetry circuitry 1852 for communicating with an implantable device, a processor 1854 and memory 1856, which may store processor-executable instructions to perform the scheduling 1802 or other methods. In the example of FIG. 18, the block 1802 indicates that a patient is typically at rest from 0 hrs to 6 hrs and that ventricular pacing, if implemented, may be disabled for a period of time per an action block 1812 to update one or more parameters.

FIG. 18 also shows another technique to commence updating of one or more parameters. A sense block 1804 senses or otherwise acquires information germane to patient activity. A decision block 1808 follows that decides, based at least in part on the sensed or otherwise acquired information, whether the patient is at rest. If the decision block 1808 decides that the patient is not at rest, then the method 1800 continues at the sense block 1804 or takes other action (e.g., a timeout, etc.). However, if the decision block 1808 decides that the patient is at rest, then the method 1800 continues in an action block 1812 that disables ventricular pacing. With ventricular pacing disabled, measurement of $DD_{RV}$, $DD_{LV}$, $AD_{RV}$ or $AD_{LV}$ may occur, per the measurement block 1816. The measurement block 1816 may measure one or more of these intervals, may measure an interval multiple times, average values, etc.

After measurement of DD interval or AD interval, an update block 1820 updates the $DD_{Rest}$ or the $AD_{Rest}$ parameter. The optional analysis 1840 may use the updated DD or AD information. After the measurement or update of the DD interval or AD interval, the method 1800 may enable ventricular pacing, however, as shown in FIG. 18, the method 1800 continues in another measurement block 1824 that measures $\Delta P$ or $\Delta A$. An update block 1828 follows for updating the $\Delta P_{Rest}$ or the $\Delta A_{Rest}$ parameter. The optional analysis 1840 may use the updated information $\Delta P$ or $\Delta A$. An action block 1832 then enables ventricular pacing.

While the method 1800 updates parameters according to patient activity level, a schedule or other mechanism may be used to call for an update to one or more parameters for use in an equation (see, e.g., Eqns. 16-19 and pacing latency of blocks 1220 and 1230 of FIG. 12).

The method 1800 may also provide for determining values for VV, for example, where bi-ventricular pacing is used or may be used. Alternatively, even if bi-ventricular pacing is not used, such information may be collected for purposes of assessing cardiac condition and optionally for assessing parameters for other patients that may benefit from bi-ventricular pacing therapies or that are already being treated with bi-ventricular pacing therapy.

Figure 19:
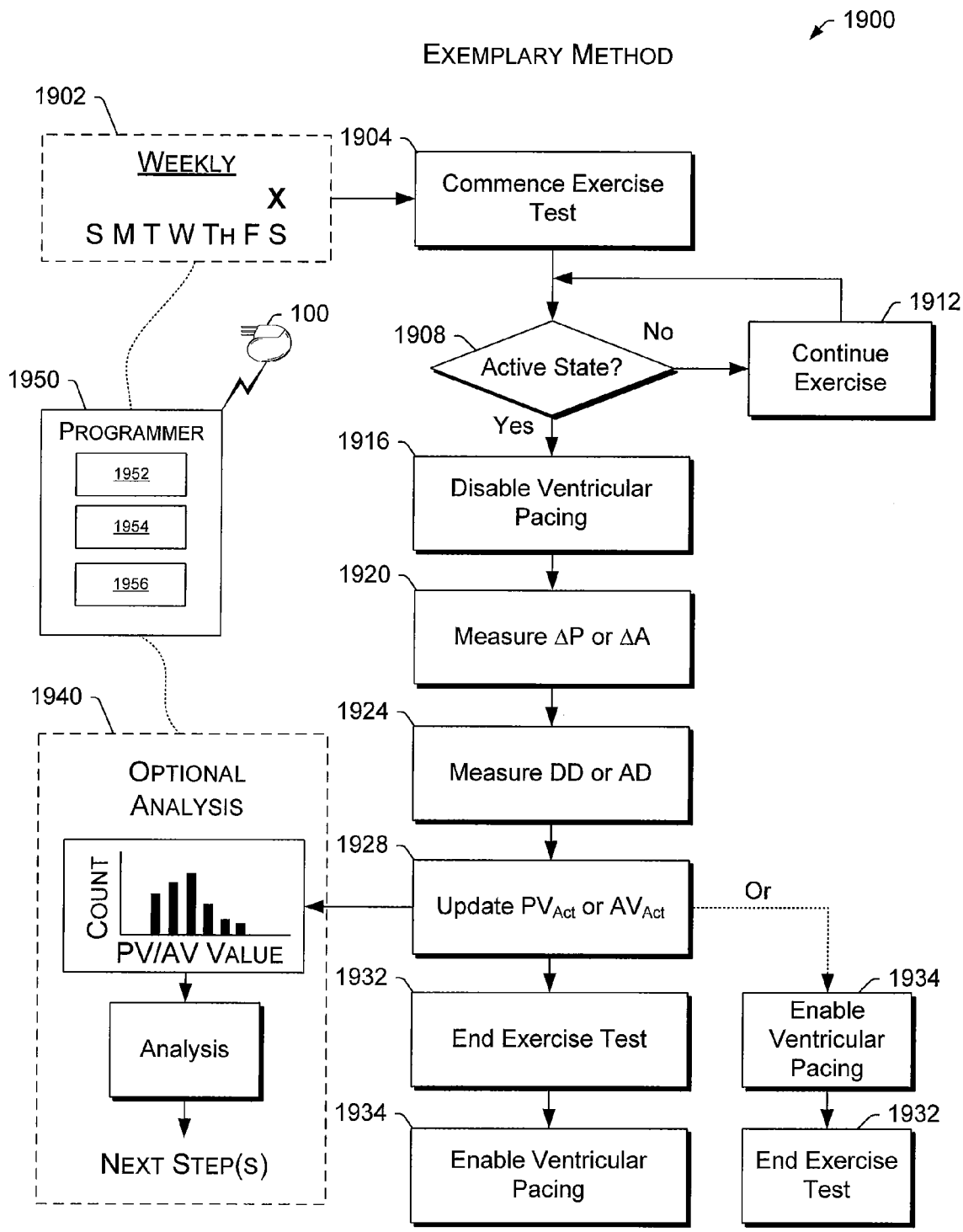
FIG. 19 is a block diagram of an exemplary method for commencing an exercise test and updating one or more parameters during the exercise test.

FIG. 19 shows an exemplary method 1900 that may be used to update one or more parameters for use in an equation to determine one or more pacing parameters. An optional analysis method 1940 may rely on one or more measures and/or an updated parameter. For example, PV or AV values may be stored as a histogram where an updated PV or AV value is added to the histogram followed by an analysis of the histogram. Such an analysis may occur on a less frequent basis than the exercise test, for example, once a month as opposed to weekly. An optional computing device 1950 configured for programming an implantable device 100 may be used to perform the analysis method 1940, for example, using information acquired from the implantable device 100 where the implantable device 100 includes control logic for implementing the method 1900. The programmer 1950 includes telemetry circuitry 1952 for communicating with an implantable device, a processor 1954 and memory 1956, which may store processor-executable instructions to perform the analysis 1940 or other methods. The programmer 1950 may include features of a commercially available programmer (e.g., the Model 3510 programmer and model 3307 software or the MERLIN™ programmer and software marketed by St. Jude Medical, Sylmar, Calif.).

The method 1900 may occur according to a schedule 1902, for example, once a week on a day set by a clinician via a programmer to program an implantable device (see, e.g., the device 100 of FIGS. 1 and 2). As shown in FIG. 19, the schedule 1902 causes a commencement block 1904 to instruct a patient to commence an exercise test (e.g., a six minute walk test, etc.). Where such a test occurs over a predetermined period of time, an exemplary method may proceed in a manner to update one or more parameters during this period of time.

The optional computing device 1950 may be used to schedule (per block 1902) an implantable device 100 where the implantable device includes control logic for implementing the method 1900. The programmer 1950 includes telemetry circuitry 1952 for communicating with an implantable device, a processor 1954 and memory 1956, which may store processor-executable instructions to perform the scheduling 1902 or other methods.

According to the method 1900, a decision block 1908 decides if the exercising patient has achieved a desired activity state. If the decision block 1908 decides that the activity state has not been reached, then a continuation block 1912 may instruct the patient to continue exercising. However, if the decision block 1908 decides that a patient has reached a particular exercise state, then the method 1900 enters an action block 1916 to disable ventricular pacing for one or both ventricles. An override mechanism may exist to enable ventricular pacing, for example, based on health risk, arrhythmia, etc. Such an override mechanism may terminate, reset or pause the method 1900.

The method 1900 includes two measurement blocks 1920, 1924 that measure $\Delta P$ or $\Delta A$ and DD or AD (e.g., $DD_{RV}$, $DD_{LV}$, $AD_{RV}$ or $AD_{LV}$), respectively. An update block 1928 follows that updates a $PV_{Act}$ or a $AV_{Act}$ pacing parameter. As shown in FIG. 19, two options exist. One option enters a termination block 1932 that ends the exercise test followed by an action block 1934 that enables ventricular pacing whereas another option enables ventricular pacing 1934 and then ends the exercise test 1932. In the latter option, the updated pacing parameter may be tested. If such testing reveals any issues or suboptimal performance, then appropriate corrective action may be taken. For example, the method may re-enter block 1908 or block 1916.

The method 1900 may also provide for determining activity state (e.g., exercise state) values of parameters associated with VV, for example, where bi-ventricular pacing is used or may be used. Alternatively, even if bi-ventricular pacing is not used, such information may be collected for purposes of assessing cardiac condition and optionally for assessing parameters for other patients that may benefit from bi-ventricular pacing therapies or that are already being treated with bi-ventricular pacing therapy.

The method 1900 may also provide for determining pacing latency for the left ventricle and/or for the right ventricle. Pacing latency may be used in correcting a PV, AV or VV delay, as described with respect to blocks 1220 and 1230 of FIG. 12.

Figure 20:
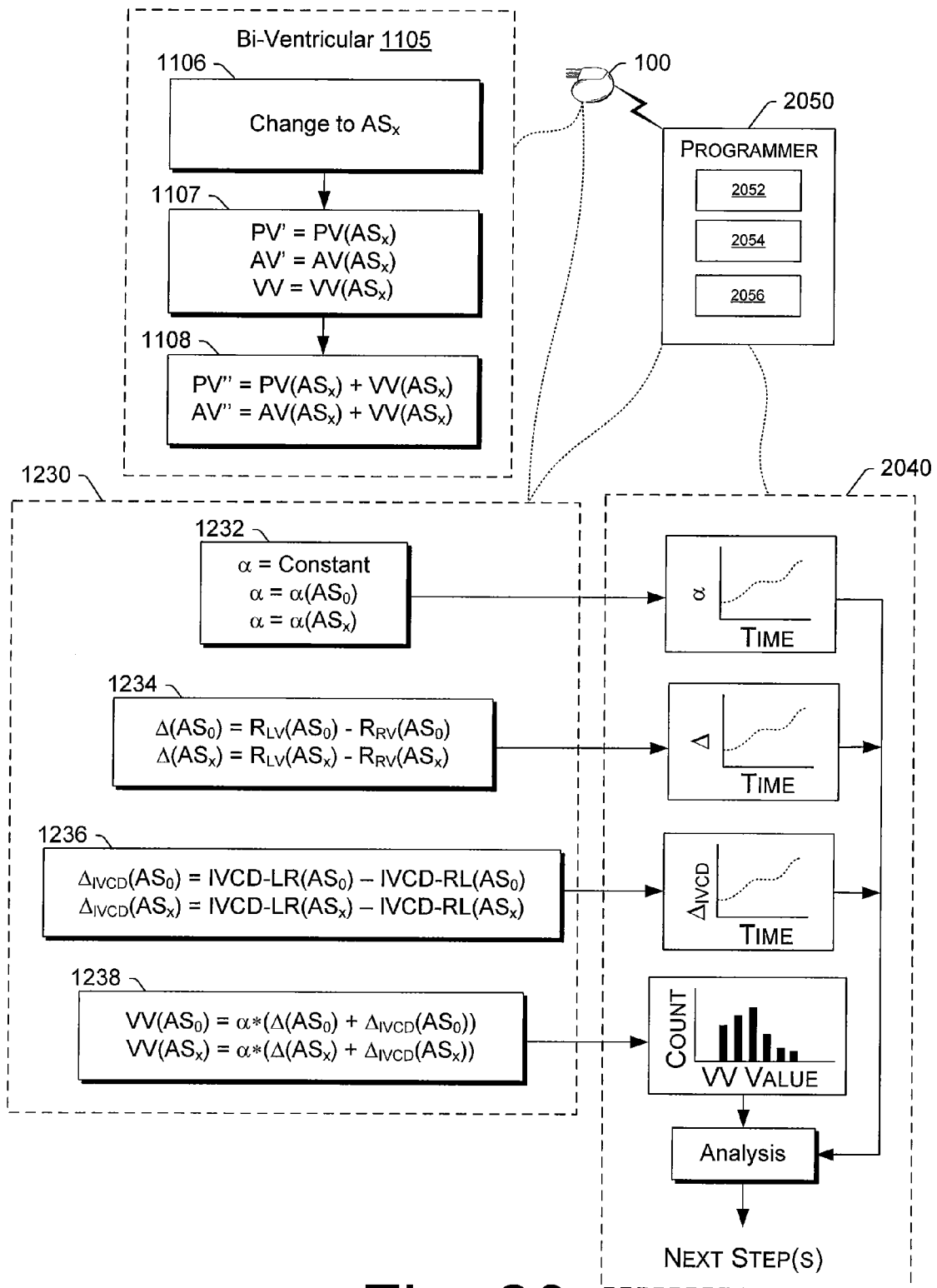
FIG. 20 is a block diagram of the method for bi-ventricular pacing of FIG. 11, the VV states of FIG. 12 and various exemplary analysis techniques that may use an external computing device and/or an implantable device such as the device of FIGS. 1 and 2.

FIG. 20 shows the method 1105 for bi-ventricular pacing of FIG. 11, the VV states 1230 of FIG. 12 and an exemplary analysis 2040 that may use an external computing device 2050 and/or an implantable device such as the device 100 of FIGS. 1 and 2. The VV states 1230 include values for an $\alpha$ parameter (block 1232), values for $\Delta$ (block 1234) values for IVCD-LR, IVCD-RL and $\Delta_{IVCD}$ (block 1236) and values for VV (block 1238). The VV block may include one or more correction terms that account for pacing latency, as described with respect to block 1230 of FIG. 12.

The analysis 2040 may include an analysis of any of the various values, for example, with respect to state, time, pacing latency, etc. The external device 2050 is optionally configured for programming the implantable device 100 and may be used to perform the analysis method 2040, for example, using information acquired from the implantable device 100 where the implantable device 100 includes control logic for acquiring any of the VV state values 1230. The programmer 2050 includes telemetry circuitry 2052 for communicating with an implantable device, a processor 2054 and memory 2056, which may store processor-executable instructions to perform the analysis 2040 or other methods. The programmer 2050 may include features of a commercially available programmer (e.g., the Model 3510 programmer and model 3307 software or the MERLIN™ programmer and software marketed by St. Jude Medical, Sylmar, Calif.).

The analysis method 1940, the analysis method 2040 or other analysis method may include comparing differences in one or more parameters or one or more measures over time for different activity states. For example, a difference may exist between PV rest and PV active at a first time. At a later time, the difference between PV rest and PV active may change. As described herein, a difference value or the nature of the change (e.g., fast or slow convergence or divergence) may be used to assess patient condition. Where a change occurs in a pacing latency, an analysis method may issue an alert or change the form of an equation to include or exclude a pacing latency correction term (e.g., for PV, AV or VV).

As described herein, techniques may be used for single ventricle pacing and/or bi-ventricular pacing. Various techniques can determine a PV delay based at least in part on P wave width and an atrio-ventricular conduction time variable such as the aforementioned DD interval, which may be a PR delay minus a P wave width (e.g., DD=PR−ΔP). As already mentioned, DD interval may change with heart rate or activities. A rest value for the DD interval ($DD_{Rest}$) may thus be calculated as $PR_{Rest}-\Delta P_{Rest}$. The parameter β may be considered a scaling factor, for example, measured at rest (e.g., $\delta/DD_{Rest}$) and the parameter δ can be set, for example, as δ=60 ms if P wave width <100 ms or 30 ms if P wave width ≧100 ms. According to this example, $PV_{Rest}$ may be $\Delta P_{Rest}$+ 60 ms or +30 ms, depending on a patient's P wave width at rest. Similarly, when the patient's activity increases, both P wave width and the DD interval could change and hence $PV_{Act}$ could be calculated as $\Delta P_{Act}+((60 \text{ ms or } 30 \text{ ms})/DD_{Rest})*DD_{Act}$.

For atrial stimulation, an AV delay may be determined using the AD parameter (e.g., AD=AR−ΔA), for example, where AD is the time delay between end of an atrial evoked response waveform and the start of a ventricular QRS complex, which may change with heart rate or activities. A rest value for the AD interval ($AD_{Rest}$) may thus be calculated as $AR_{Rest}-\Delta A_{Rest}$. The parameter β may be considered a scaling factor, for example, measured at rest (e.g., $\delta/AD_{Rest}$) and the parameter δ can be set, for example, as δ=60 ms if A wave width <150 ms or 30 ms if A wave width 150 ms. According to this example, $AV_{Rest}$ may be $\Delta A_{Rest}$+60 ms or +30 ms, depending on a patient's A wave width at rest. Similarly, when the patient's activity increases, both A wave width and the AD interval could change and hence $AV_{Act}$ could be calculated as $\Delta A_{Act}+((60 \text{ ms or } 30 \text{ ms})/AD_{Rest})*AD_{Act}$.

Recent clinical data indicates that during exercise, optimal PV/AV delays are prolonged compared with those at rest in HF patients. Various exemplary techniques described herein can account for changes for HF patients during exercise and at rest through the duration of P wave or A wave and an appropriate atrio-ventricular conduction delay. During exercise some HF patients may have an increase in width of atrial signals or atrio-ventricular conduction delays or both that would lead to prolonged optimal AV and PV delays. In patients with normal rate responses, AV or PV delays may have negative hysteresis or remain the same as at rest.

Various exemplary techniques use rate adaptive an AV delay or a PV delay where tests occur at rest and during exercise and where an exemplary implantable device stores data. An implantable device may perform such tests according to a schedule, an event, etc., or such tests may be performed under guidance from a care provider, for example, during an office visit. Various exemplary techniques use one or more activity sensors to determine an optimal AV or PV delay and/or an optimal VV delay. Various exemplary techniques can update, for example, optimal AV or PV delay and/or VV delay at one or more activity states (e.g., rest, exercise, etc.). Interpolation of test data may occur to select an optimal AV or PV delay and/or VV delay for one or more activity states other than those tested.

Where a patient has an RV lead in an outflow tract and a therapy that relies on LV pacing only, for the RV lead in right ventricular outflow tract or high septum, the VV delay may be determined as follows: $VV=\alpha*(|\Delta|+\Delta_{IVCD})$, where α~0.5. However the interpolation of a may be different from that with RV lead in RV apex. Where LV only pacing occurs, $PV_{LV}=PR_{RV}-VV$ where $VV=(|\Delta|+\Delta_{IVCD})$, which does not rely on the parameter α.

An exemplary method may analyze parameters over time, for example, in relationship to patient activity. As already mentioned, heart failure patients exhibit certain characteristics for P wave width or A wave width or DD interval or AD interval (e.g., $DD_{RV}$, $DD_{LV}$, $AD_{RV}$, $AD_{LV}$). Such an analysis may be used to track patient condition and possibly progression of heart failure (worsening or improving). In turn, such an analysis may be used to select or tailor a patient therapy.

An exemplary implantable device includes control logic to determine a rest state atrio-ventricular delay (e.g., PV rest or AV rest) based on width of an atrial event (e.g., ΔP or ΔA) as measured during a patient rest state and based on a value of a parameter δ that depends on one or more characteristics of the atrial event and control logic to determine an active state atrio-ventricular delay (e.g., PV active or AV active) based at least in part on a rest state interval (e.g., DD rest or AD rest) measured during a patient rest state and an active state interval (e.g., DD active or AD active) measured during a patient active state where such intervals extend from the end of a respective atrial event to the beginning of a respective ventricular QRS complex or a point within a respective ventricular QRS complex.

Such an exemplary method may include initiating pacing therapy where the therapy uses PV rest, PV active, AV rest or AV active (or other parameters described herein). Such initiating may include calling for commencement of therapy or adjusting one or more parameters of a therapy that has already been commenced or otherwise implemented (e.g., programmed "on"). Initiation of a therapy can be accomplished using instructions (e.g., stored on a computer-readable medium) that cause a processor to initiate certain action or actions. Such action may cause a device to actually deliver a therapy (e.g., a pacing therapy).

An exemplary method may include determining a patient rest state PV delay (PV rest) based on a P wave width (ΔP rest) measured during a patient rest state and a value of a parameter δ where the value of the parameter δ depends on the P wave width (ΔP rest) and determining a patient active state PV delay (PV active) based at least in part on an atrio-ventricular delay (DD rest) measured during the patient rest state and an atrio-ventricular delay (DD active) measured during a patient active state wherein the atrio-ventricular delays extend from the end of a respective P wave to the beginning of a respective ventricular QRS complex or a point within a respective ventricular QRS complex.

Where a therapy includes atrial pacing, an exemplary method may include determining a patient rest state AV delay (AV rest) based on an A wave width (ΔA rest) measured during a patient rest state and a value of a parameter δ where the value of the parameter δ depends on the A wave width (ΔA rest) and determining a patient active state AV delay (AV active) based at least in part on an atrio-ventricular delay (AD rest) measured during the patient rest state and an atrio-ventricular delay (AD active) measured during a patient active state where the atrio-ventricular delays extend from the end of a respective A wave to the beginning of a respective ventricular QRS complex or a point within a respective ventricular QRS complex.

As already described, an exemplary method may include sensing patient activity and, based on the sensed patient activity, selecting PV rest or PV active or AV rest or AV active, as appropriate. Such intervals may be determined for a single ventricle or both ventricles. Where both ventricles are paced, an exemplary method may determine a time to pace the other ventricle based on PV or AV and an interventricular delay (VV). As described (see, e.g., FIG. 9), an interventricular delay (VV) may depend at least in part on an interventricular conduction delay (IVCD) or a difference between two IVCDs ($\Delta_{IVCD}$).

As already mentioned, PV active may be equal to ΔP active plus δ multiplied by the ratio of DD active to DD rest and AV active may be equal to ΔA active plus δ multiplied by the ratio of AD active to AD rest. While various methods use a ΔP or ΔA from an active state, an exemplary method may use a rest state ΔP or ΔA and optionally an associated δ value.

An exemplary method may compare PV rest or AV rest to a PR interval or AR interval measured during a patient rest state. As already explained, a method may use PV rest if PV rest is less than the PR interval measured during a patient rest state and likewise, a method may use AV rest if AV rest is less than the AR interval (or PR interval) measured during a patient rest state. Similar comparisons may occur for active states.

In instances where ventricular pacing occurs, an exemplary method may include disabling pacing to at least one ventricle prior to measuring DD rest or DD active and/or enabling pacing to at least one ventricle after measuring DD rest or DD active. For atrial activation, similar disabling and enabling may occur with respect to AD rest or AD active. If pacing occurs for both ventricles (i.e., bi-ventricular pacing) then a method may include disabling or enabling pacing to both ventricles prior to measuring or after measuring, respectively.

As explained above, the parameter δ is typically a time delay and its value may be determined using a state-based relationship between ΔP or ΔA and the parameter δ or an equation may be used to determine a value of the parameter δ based on ΔP or ΔA.

An exemplary method includes acquiring, via an implantable device, at least one of ΔP, ΔA, PV rest, AV rest, PV active, AV active, DD rest, AD rest, DD active AD active and δ where the implantable device includes control logic to determine PV rest or AV rest based on ΔP or ΔA measured during a patient rest state and a value of a parameter δ where the value of the parameter δ depends on ΔP or ΔA and to determine PV active or AV active based at least in part on DD rest or AD rest measured during a patient rest state and DD active or AD active measured during a patient active state where DD or AD extend from the end of a respective P wave or A wave to the beginning of a respective ventricular QRS complex or a point within a respective ventricular QRS complex and assessing patient condition based at least in part on at least one of ΔP, ΔA, PV rest, AV rest, PV active, AV active, DD rest, AD rest, DD active AD active and δ. In such a method, the assessment may assess heart condition, for example, heart failure. Such an assessment may compare values over time, compare values for different activity states or a combination thereof.

An exemplary method may include acquiring, via an implantable device, an interventricular conduction delay from the left ventricle to the right ventricle (IVCD-LR) and/or an interventricular conduction delay from the right ventricle to the left ventricle (IVCD-RL) and assessing patient condition based at least in part on the IVCD-LR and/or IVCD-RL. In such a method, the IVCD-LR and/or the IVCD-RL may correspond to a particular activity state. An exemplary method may include acquiring, via an implantable device, an interventricular delay (VV) and assessing patient condition based at least in part on the VV. In such a method, the VV may correspond to a particular activity state.

An exemplary method includes determining for a ventricle PV rest or AV rest based on ΔP or ΔA, respectively, measured during a patient rest state and a value of a parameter δ where the value of the parameter δ depends on ΔP or ΔA, determining for the ventricle PV active or AV active based at least in part on DD rest or AD rest, respectively, measured during a patient rest state and DD active or AD active, respectively, measured during a patient active state where DD or AD extend from the end of a respective P wave or A wave to the beginning of a respective ventricular QRS complex or a point within a respective ventricular QRS complex and determining PV or AV for the other ventricle based at least in part on an interventricular delay (VV). In such a method, VV may depend on activity state. For example, a method may determine or provide VV rest and VV active. In various methods, VV may depend at least in part on an interventricular conduction delay (IVCD) and the IVCD, whether IVCD-RL or IVCD-LR, may depend on activity state. As described above, VV may depend on a parameter α, which optionally depends on or corresponds to activity state.

A method may assess patient condition based on at least one of PV, AV and VV where PV and AV correspond to an activity state and optionally where VV corresponds to an activity state. A method may assess patient condition based at least in part on at least one of DD, AD, ΔP, ΔA and IVCD where DD and AD correspond to an activity state and optionally where IVCD, ΔP and/or ΔA correspond to an activity state. Patient or cardiac condition may be assessed using other measures such as impedance, evoked response characteristics, etc. In particular, measures that reflect heart failure may be useful.

An exemplary computing device may include a processor, memory, telemetry circuitry for communicating with an implantable device and control logic to assess cardiac condition. The assessment of cardiac condition may be based on any of a variety of measures or parameters discussed herein. In particular, such an assessment may use information from one or more activity states. For example, an assessment may be based at least in part on information acquired from an implantable device where the information includes at least one of PV rest, AV rest, PV active, AV active, DD rest, AD rest, DD active AD active and δ. Such an implantable device may include control logic to determine PV rest or AV rest based on ΔP or ΔA measured during a patient rest state and a value of a parameter δ where the value of the parameter δ depends on ΔP or ΔA and to determine PV active or AV active based at least in part on DD rest or AD rest measured during a patient rest state and DD active or AD active measured during a patient active state where DD or AD extend from the end of a respective P wave or A wave to the beginning of a respective ventricular QRS complex or a point within a respective ventricular QRS complex.

While various examples mention use of a "rest" state, a rest state may be a base state. Alternatively, a base state may be a state other than a rest state. For example, a base state may correspond to a low activity state where a patient performs certain low energy movements (e.g., slow walking, swaying, etc.) that may be encountered regularly throughout a patient's day. Thus, a base state may be selected as a commonly encountered state in a patient's waking day, which may act to minimize adjustments to PV, AV or VV. Further, upon entering a sleep state, a device may turn off adjustments to PV, AV or VV and assume sleep state values for PV, AV or VV. Such decisions may be made according to a timer, a schedule, an activity sensor, etc.

Various examples may use a correction term based at least in part on a pacing latency. For example, an exemplary method includes determining a PV delay based on a P wave width and a value of a parameter δ where the value of the parameter δ depends on the P wave width, determining a pacing latency for a ventricle, adjusting the PV delay by subtracting the pacing latency from the PV delay and calling for delivery of stimulation energy to the ventricle using the adjusted PV delay (see, e.g., block 1220 of FIG. 12). Where atrial pacing occurs, an exemplary method includes determining an AV delay based on an A wave width and a value of a parameter δ where the value of the parameter δ depends on the A wave width, determining a pacing latency for a ventricle, adjusting the AV delay by subtracting the pacing latency from the AV delay and calling for delivery of stimulation energy to the ventricle using the adjusted AV delay (see, e.g., block 1220 of FIG. 12). Where bi-ventricular pacing occurs, an exemplary method includes providing a standard pacing latency, determining a pacing latency for a ventricle, determining a correction term by subtracting the pacing latency from the standard pacing latency, correcting a VV delay by subtracting the correction term from the VV delay and calling for delivery of stimulation energy to a ventricle using the corrected VV delay (see, e.g., block 1230 of FIG. 12).

An exemplary computing device may include control logic to assess cardiac condition based at least in part on information acquired from an implantable device where the information comprises at least one member selected from a group consisting of $\alpha$, $\Delta$, IVCD-RL, IVCD-LR, $\Delta_{IVCD}$ and VV. The computing device may be the implantable device, or in other words, an implantable device may be capable of assessing patient condition and more particularly cardiac condition.

Various exemplary methods may be implementable wholly or to varying extent using one or more computer-readable media that include processor executable instructions for performing one or more actions. For example, the device 100 of FIG. 2 shows various modules associated with a processor 220. Hence, a module may be developed using an algorithm described herein. Such a module may be downloadable to an implantable device using a device programmer (e.g., 1850, 1950, 2050) or may be incorporated into a device during manufacture by any of a variety of techniques. At times such instructions are referred to as control logic.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method comprising:
   measuring a P wave width ($\Delta P$ base) during a patient base state;
   determining a patient base state PV delay (PV base) based on the P wave width ($\Delta P$ base) and a value of a parameter δ wherein the value of the parameter δ depends on the P wave width ($\Delta P$ base);
   measuring an atrio-ventricular delay (DD base) during the patient base state;
   measuring an atrio-ventricular delay (DD active) during a patient active state;
   determining a patient active state PV delay (PV active) based at least in part on the atrio-ventricular delay (DD base) and the atrio-ventricular delay (DD active) wherein the atrio-ventricular delays extend from the end of a respective P wave to the beginning of a respective ventricular QRS complex or a point within a respective ventricular QRS complex; and
   applying a pacing therapy that uses PV base or PV active.

2. The method of claim 1 further comprising:
   sensing patient activity; and
   based on the sensed patient activity, selecting the PV base or the PV active.

3. The method of claim 1 wherein the determining determines the PV active for pacing the left ventricle or for pacing the right ventricle.

4. The method of claim 1 wherein the parameter δ comprises a time delay.

* * * * *